US007037506B2

(12) United States Patent
Kuo

(10) Patent No.: US 7,037,506 B2

(45) Date of Patent: *May 2, 2006

(54) VACCINE ACCELERATOR FACTOR (VAF) FOR IMPROVEMENT OF VACCINATIONS IN POULTRY

(75) Inventor: Tsun Yung Kuo, I-Lan (TW)

(73) Assignee: Schweltzer Chemical Corporation Ltd., Taipei (TW)

(*) Notice: Subject to any disclaimer, the term of this patent is extended or adjusted under 35 U.S.C. 154(b) by 19 days.

This patent is subject to a terminal disclaimer.

(21) Appl. No.: 10/429,735

(22) Filed: May 6, 2003

(65) Prior Publication Data

US 2003/0207836 A1 Nov. 6, 2003

Related U.S. Application Data

(63) Continuation-in-part of application No. 10/377,718, filed on Mar. 4, 2003.

(60) Provisional application No. 60/362,547, filed on Mar. 8, 2002.

(51) Int. Cl.
*A61K 39/12* (2006.01)
*A61K 39/295* (2006.01)

(52) U.S. Cl. ............................... 424/199.1; 424/202.1; 424/204.1; 424/214.1; 424/229.1; 424/222.1; 424/216.1; 424/207.1; 424/211.1; 424/225.1; 424/233.1; 424/232.1; 435/235.1; 435/320.1; 514/44

(58) Field of Classification Search .................. 514/44; 536/23.72; 435/320.1, 235.1, 91.41; 424/199.1, 424/204.1, 214.1, 202.1, 229.1, 222.1, 216.1, 424/207.1, 232.1, 211.1, 225.1, 233.1
See application file for complete search history.

(56) References Cited

U.S. PATENT DOCUMENTS

| | | | | |
|---|---|---|---|---|
| 4,458,630 | A | 7/1984 | Sharma et al. | |
| 5,056,464 | A | 10/1991 | Lewis | |
| 5,397,568 | A | 3/1995 | Whitfill et al. | |
| 5,397,569 | A | 3/1995 | Whitfill et al. | |
| 5,595,912 | A | 1/1997 | Vakharia et al. | |
| 5,643,578 | A | 7/1997 | Robinson et al. | |
| 5,699,751 | A | 12/1997 | Phelps et al. | |
| 5,750,101 | A | 5/1998 | Stone | |
| 5,780,289 | A | 7/1998 | Vermeulen et al. | |
| 5,817,320 | A | 10/1998 | Stone | |
| 5,871,748 | A | 2/1999 | Whitfill et al. | |
| 6,032,612 | A | 3/2000 | Williams | |
| 6,048,535 | A * | 4/2000 | Sharma | 424/202.1 |
| 6,136,319 | A | 10/2000 | Whitfill et al. | |
| 6,221,362 | B1 * | 4/2001 | Audonnet et al. | 424/199.1 |
| 6,286,455 | B1 | 9/2001 | Williams | |
| 6,299,874 | B1 | 10/2001 | Whitfill et al. | |
| 6,322,780 | B1 | 11/2001 | Lee et al. | |

FOREIGN PATENT DOCUMENTS

WO WO 98/03659 * 1/1998

OTHER PUBLICATIONS

Rollier et al (Vaccine 18:3091-3096,2000).*
Kodihalli et al (Journal of Virology 71:3391-3396, 1997).*
Oshop et al (Veterinary Immunology and Immunopathology 89:1-12, published Oct. 8, 2002).*
Reddy et al (Vaccine 14:469-477, 1996).*
deLeeuw et al (Journal of General Virology 80:131-136, 1999).*
Zimmerman, Stefan et al., Immunostimulatory DNA as adjuvant: efficacy of phosphodiester CpG oligonucleotides is enhanced by 3' sequence modifications; Vaccine, vol. 21, pp. 990-995, 2003.
Johnston, P.A. et al., Applications in In Ovo Technology, Poultry Science, vol. 76, pp. 165-178, 1997.

* cited by examiner

*Primary Examiner*—Mary E. Mosher
(74) *Attorney, Agent, or Firm*—Pai Patent & Trademark Law Firm

(57) ABSTRACT

The present invention provides a vaccine accelerator factor (VAF) which is an in ovo nucleotide immuno-stimulant. The VAF contains one or more DNA constructs, each having a DNA molecule and a vector. Each of the DNA molecule contains one or more genes or gene fragments, each encoding an antigenic peptide of an avian virus. The VAF is preferably administered to the amniotic fluid of an egg after being fertilized for about 17–19 days. The VAF can be co-administered with a viral vaccine containing one or more attenuated or inactive avian viruses. Alternatively, the VAF can be administered prior to the administration of the viral vaccine, which is administered at hatch or post-hatch. The VAF stimulates and accelerate a protective immune response of a viral vaccine.

24 Claims, No Drawings

SEQUENCE LISTING

```
<160> NUMBER OF SEQ ID NOS: 19

<210> SEQ ID NO 1
<211> LENGTH: 3650
<212> TYPE: DNA
<213> ORGANISM: Marek's disease virus

<400> SEQUENCE: 1

tcgagctcgc cggggatgtt tagtcacgat agacatcggt tcgcccagcc gtcgaataca      60

gcattatatt ttagtgttga aaatgtaggg ctgcttcctc acttaaagga ggaaatggct     120

cgattcatgt ttcatagcag tagaaaaaca gattggaccg tcagtaagtt tagagggttt     180

tatgacttta gcactataga taatgtaact gcggcccatc gcatggcttg gaaatatatc     240

aaagaactga tttttgcaac agctttattt tcttctgtat ttaaatgtgg cgaattgcac     300

atctgtcgtg ccgacagttt gcagatcaac agcaatggag actatgtatg gaaaaatgga     360

atatatataa catatgaaac cgaatatcca cttataatga ttctggggtc agaatcaagc     420

acttcagaaa cgcaaaatat gactgcaatt attgatacag atgtttttc gttgctttat      480

tctattttgc agtatatggc ccccgttacg gcagatcagg tgcgagtaga acagattacc     540

aacagccacg cccccatctg acccgtccaa tattcttgtg tccctgcatt ttatctcaca     600

caatttatga acagcatcat taagatcatc tcactatgca ctattttagg cggaattgca     660
```

-continued

```
ttttttttcct tatagttatt ctatatggta cgaactcatc tccgagtacc caaaatgtga    720
catcaagaga agttgtttcg agcgtccagt tgtctgagga agagtctacg ttttatcttt    780
gtcccccacc agtgggttca accgtgatcc gtctagaacc gccgcgaaaa tgtcccgaac    840
ctagaaaagc caccgagtgg ggtgaaggaa tcgcgatatt atttaaagag aatatcagtc    900
catataaatt taaagtgacg ctttattata aaaatatcat tcagacgacg acatggacgg    960
ggacgacata tagacagatc actaatcgat atacagatag gacgcccgtt tccattgaag   1020
agatcacgga tctaatcgac ggcaaaggaa gatgctcatc taaagcaaga taccttagaa   1080
acaatgtata tgttgaagcg tttgacaggg atgcgggaga aaaacaagta cttctaaaac   1140
catcaaaatt caacacgccc gaatctaggg catggcacac gactaatgag acgtataccg   1200
tgtggggatc accatggata tatcgaacgg gaacctccgt caattgtata gtagaggaaa   1260
tggatgcccg ctctgtgttt ccgtattcat attttgcaat ggccaatggc gacatcgcga   1320
acatatctcc attttatggt ctatccccac cagaggctgc cgcagaaccc atgggatatc   1380
cccaggataa tttcaaacaa ctagatagct atttttcaat ggatttggac aagcgtcgaa   1440
aagcaagcct tccagtcaag cgtaactttc tcatcacatc acacttcaca gttgggtggg   1500
actgggctcc aaaaactact cgtgtatgtt caatgactaa gtggaaagag gtgactgaaa   1560
tgttgcgtgc aacagttaat gggagataca gatttatggc ccgtgaactt tcggcaacgt   1620
ttatcagtaa tacgactgag tttgatccaa atcgcatcat attaggacaa tgtattaaac   1680
gcgaggcaga agcagcaatc gagcagatat ttaggacaaa atataatgac agtcacgtca   1740
aggttggaca tgtacaatat ttcttggctc tcggggggatt tattgtagca tatcagcctg   1800
ttctatccaa atccctggct catatgtacc tcagagaatt gatgagagac aacaggaccg   1860
atgagatgct cgacctggta aacaataagc atgcaattta taagaaaaat gctacctcat   1920
tgtcacgatt gcggcgagat attcgaaatg caccaaatag aaaaataaca ttagacgaca   1980
ccacagctat taaatcgaca tcgtctgttc aattcgccat gctccaattt ctttatgatc   2040
atatacaaac ccatattaat gatatgttta gtaggattgc cacagcttgg tgcgaattgc   2100
agaatagaga acttgtttta tggcacgaag ggataaagat taatcctagc gctacagcga   2160
gtgcaacatt aggaaggaga gtggctgcaa agatgttggg ggatgtcgct gctgtatcga   2220
gctgcactgc tatagatgcg gaatccgtca ctttgcaaaa ttctatgcga gttatcacat   2280
ccactaatac atgttatagc cgaccattgg ttctattttc atatggagaa aaccaaggaa   2340
acatacaggg acaactcggt gaaaacaacg agttgcttcc aacgctagag gctgtagagc   2400
catgctcggc taatcatcgt agatattttc tgtttggatc cggttatgct ttatttgaaa   2460
actataattt tgttaagatg gtagacgctg ccgatataca gattgctagc acatttgtcg   2520
agcttaatct aaccctgcta gaagatcggg aaattttgcc tttatccgtt tacacaaaag   2580
aagagttgcg tgatgttggt gtattggatt atgcagaagt agctcgccgc aatcaactac   2640
atgaacttaa attttatgac ataaacaaag taatagaagt ggatacaaat tacgcgttta   2700
tgaacggttt ggccgaattg tttaacggta tgggtcaggt agggcaagct ataggcaaag   2760
ttgtagtagg ggctgccggt gcaatcgtat ctaccatatc tggtgtctct gctttcatgt   2820
caatcccttt ggggctttcg gcaatcggtt taatcattat agcaggactc gtggctgcat   2880
ttttagcata tcgttatgta aacaagctta aaagcaatcc aatgaaagcc ctttatccta   2940
tgacaacaga agtgcttaag gcacaggcaa cgcgtgagtt gcatggcgag gaatcagatg   3000
```

-continued

```
atttggaacg aacatctatt gatgaaagaa aattagaaga agctagagaa atgataaaat   3060

atatggcgtt agtctccgcg gaagaacgcc acgagaaaaa actgcggaga aagaggcgag   3120

gcactaccgc cgttctatcg gaccacctgg caaaaatgag gattaaaaat agtaacccta   3180

aatatgataa gttacctact acatattcag actcagaaga tgatgctgtg taagtgggca   3240

ctattatatt tgaactgaat aaaacgcata gagcatgata tggtttactc atttattgcg   3300

agatataaag catattcaat acgatatatt gcgaacgtga tgctaaaaac atagctccct   3360

gtattattga tgcgccatca tttgattaat aaatacatcg acgccggcat cactggtgcg   3420

gtgtatacca gctacggcgc tagcattcat ggtatcccgt gattgctcga tgctttcctt   3480

ctgaattccg tcggaacgct cctgagagat ggtcgcagtt attggtacat ttcgaccagc   3540

ctccggatct gaaactggca caggaatgca ccgtggaatt ggtagaagtt tttccttccg   3600

tggaaggcat agggcgttcg actcccatgg gccatgaaac tgtgggatgt              3650
```

```
<210> SEQ ID NO 2
<211> LENGTH: 3004
<212> TYPE: DNA
<213> ORGANISM: infectious bursal disease virus (IBDV)

<400> SEQUENCE: 2

tgatgccaac aaccggaccg gcgtccattc cggacgacac cctggagaag cacactctca     60

ggtcagagac ctcgacctac aatttgactg tgggggacac agggtcaggg ctaattgtct    120

ttttccctgg attccctggc tcaattgtgg gtgctcacta cacactgcag agcaatggga    180

actacaagtt cgatcagatg ctcctgactg cccagaacct accggccagt tacaactact    240

gcaggctagt gagtcggagt ctcacagtga ggtcaagcac acttcctggt ggcgtttatg    300

cactaaacgg caccataaac gccgtgacct tccaaggaag cctgagtgaa ctgacagatg    360

ttagctacaa tgggttgatg tctgcaacag ccaacatcaa cgacaaaatt gggaacgtcc    420

tagtagggga aggggtcacc gtcctcagct tacccacatc atatgatctt gggtatgtga    480

ggcttggtga ccccattccc gcaatagggc ttgacccaaa aatggtagcc acatgtgaca    540

gcagtgacag gcccagagtc tacaccataa ctgcagccga tgattaccaa ttctcatcac    600

agtaccaacc aggtggggta acaatcacac tgttctcagc caacattgat gccatcacaa    660

gcctcagcgt tgggggagag ctcgtgtttc gaacaagcgt ccacggcctt gtactgggcg    720

ccaccatcta cctcataggc tttgatggga caacggtaat caccagggct gtggccgcaa    780

acactgggct gacgaccggc accgacaacc ttatgccatt caatcttgtg attccaacaa    840

acgagataac ccagccaatc acatccatca aactggagat agtgacctcc aaaagtggtg    900

gtcaggcagg ggatcagatg ttatggtcgg caagagggag cctagcagtg acgatccatg    960

gtggcaacta tccaggggcc ctccgtcccg tcacgctagt ggcctacgaa agagtggcaa   1020

caggatccgt cgttacggtc gctggggtga gcaacttcga gctgatccca aatcctgaac   1080

tagcaaagaa cctggttaca gaatacggcc gatttgaccc aggagccatg aactacacaa   1140

aattgatact gagtgagagg gaccgtcttg gcatcaagac cgtctggcca acaagggagt   1200

acactgactt tcgtgaatac ttcatggagg tggccgacct caactctccc ctgaagattg   1260

caggagcatt cggcttcaaa gacataatcc gggccataag gaggatagct gtgccggtgg   1320

tctccacatt gttcccacct gccgctcccc tagcccatgc aattggggaa ggtgtagact   1380

acctgctggg cgatgaggca caggctgctt caggaactgc tcgagccgcg tcaggaaaag   1440
```

-continued

```
caagagctgc ctcaggccgc ataaggcagc tgactctcgc cgccgacaag gggtacgagg   1500
tagtcgcgaa tctattccag gtgccccaga atcccgtagt cgacgggatt cttgcttcac   1560
ctggggtact ccgcggtgca cacaacctcg actgcgtgtt aagagagggt gccacgctat   1620
tccctgtggt tattacgaca gtggaagacg ccatgacacc caaagcattg aacagcaaaa   1680
tgtttgctgt cattgaaggc gtgcgagaag acctccaacc tccatctcaa agaggatcct   1740
tcatacgaac tctctctgga cacagagtct atggatatgc tccagatggg gtacttccac   1800
tggagactgg gagagactac accgttgtcc caatagatga tgtctgggac gacagcatta   1860
tgctgtccaa agatcccata cctcctattg tgggaaacag tggaaatcta gccatagctt   1920
acatggatgt gtttcgaccc aaagtcccaa tccatgtggc tatgacggga gccctcaatg   1980
cttgtggcga gattgagaaa gtaagcttta gaagcaccaa gctcgccact gcacaccgac   2040
ttggccttaa gttggctggt cccggagcat tcgatgtaaa caccgggccc aactgggcaa   2100
cgttcatcaa acgtttccct cacaatccac gcgactggga caggctcccc tacctcaacc   2160
taccatacct tccacccaat gcaggacgcc agtaccacct tgccatggct gcatcagagt   2220
tcaaagagac ccccgaactc gagagtgccg tcagagcaat ggaagcagca gccaacgtgg   2280
acccactatt ccaatctgca ctcagtgtgt tcatgtggct ggaagagaat gggattgtga   2340
ctgacatggc caacttcgca ctcagcgacc cgaacgccca tcggatgcga aattttcttg   2400
caaacgcacc acaagcaggc agcaagtcgc aaagggccaa gtacgggaca gcaggctacg   2460
gagtggaggc tcggggcccc acaccagagg aagcacagag ggaaaaagac acacggatct   2520
caaagaagat ggagaccatg ggcatctact ttgcaacacc agaatgggta gcactcaatg   2580
ggcaccgagg gccaagcccc ggccagctaa agtactggca gaacacacga gaaataccgg   2640
acccaaacga ggactatcta gactacgtgc atgcagagaa gagccggttg gcatcagaag   2700
aacaaatcct aagggcagct acgtcgatct acggggctcc aggacaggca gagccacccc   2760
aagctttcat agacgaagtt gccaaagtct atgaaatcaa ccatggacgt ggcccaaacc   2820
aagaacagat gaaagatctg ctcttgactg cgatggagat gaagcatcgc aatcccaggc   2880
gggctctacc aaagcccaag ccaaaaccca atgctccaac acagagaccc cctggtcggc   2940
tgggccgctg gatcaggacc gtctctgatg aggaccttga gtgaggctcc tggaagtctc   3000
ccga                                                                3004
```

<210> SEQ ID NO 3
<211> LENGTH: 15186
<212> TYPE: DNA
<213> ORGANISM: Newcastle disease virus (NDV)

<400> SEQUENCE: 3

```
accaaacaga gaatccgtga gttacgataa aaggcgaagg agcaattgaa gtcgcacggg     60
tagaaggtgt gaatctcgag tgcgagcccg aagcacaaac tcgagaaagc cttctgccaa    120
catgtcttcc gtatttgatg agtacgaaca gctcctcgcg gctcagactc gccccaatgg    180
agctcatgga gggggagaaa aagggagtac cttaaaagta gacgtcccgg tattcactct    240
taacagtgat gacccagaag atagatggag ctttgtggta ttctgcctcc ggattgctgt    300
tagcgaagat gccaacaaac cactcaggca aggtgctctc atatctcttt tatgctccca    360
ctcacaggta atgaggaacc atgttgccat tgcagggaaa cagaatgaag ccacattggc    420
cgtgcttgag attgatggct ttgccaacgg cacgccccag ttcaacaata ggagtggagt    480
gtctgaagag agagcacaga gatttgcgat gatagcagga tctctccctc gggcatgcag    540
```

-continued

```
caacggaacc ccgttcgtca cagccggggc agaagatgat gcaccagaag acatcaccga    600
taccctggag aggatcctct ctatccaggc tcaagtatgg gtcacagtag caaaagccat    660
gactgcgtat gagactgcag atgagtcgga aacaaggcga atcaataagt atatgcagca    720
aggcagggtc caaaagaaat acatcctcta ccccgtatgc aggagcacaa tccaactcac    780
gatcagacag tctcttgcag tccgcatctt tttggttagc gagctcaaga gaggccgcaa    840
cacggcaggt ggtacctcta cttattataa cctggtaggg gacgtagact catacatcag    900
gaataccggg cttactgcat tcttcttgac actcaagtac ggaatcaaca ccaagacatc    960
agcccttgca cttagtagcc tctcaggcga catccagaag atgaagcagc tcatgcgttt   1020
gtatcggatg aaaggagata atgcgccgta catgacatta cttggtgata gtgaccagat   1080
gagctttgcg cctgccgagt atgcacaact ttactccttt gccatgggta tggcatcagt   1140
cctagataaa ggtactggga aataccaatt tgccagggac tttatgagca catcattctg   1200
gagacttgga gtagagtacg ctcaggctca gggaagtagc attaacgagg atatggctgc   1260
cgagctaaag ctaaccccag cagcaatgaa gggcctggca gctgctgccc aacgggtctc   1320
cgacgatacc agcagcatat acatgcctac tcaacaagtc ggagtcctca ctgggcttag   1380
cgaggggggg tcccaagctc tacaaggcgg atcgaataga tcgcaagggc aaccagaagc   1440
cggggatggg gagacccaat tcctggatct gatgagagcg gtagcaaata gcatgaggga   1500
ggcgccaaac tctgcacagg gcactcccca atcggggcct cccccaactc ctgggccatc   1560
ccaagataac gacaccgact gggggtattg atggacaaaa cccagcctgc ttccacaaaa   1620
acatcccaat gccctcaccc gtagtcgacc cctcgatttg cggctctata tgaccacacc   1680
ctcaaacaaa catcccctc tttcctccct cccctgctg tacaactccg cacgccctag   1740
ataccacagg cacaatgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaagacaa ccccgatcga caggacagat   2100
ctgacaaaca accatccaca cccgagcaaa cgaccccgca tgacagcccg ccggccacat   2160
ccgccgacca gccccccacc caggccacag acgaagccgt cgacacacag ttcaggaccg   2220
gagcaagcaa ctctctgctg ttgatgcttg acaagctcag caataaatcg tccaatgcta   2280
aaaagggccc atggtcgagc cccaagaggg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaacccct catgctctcc gatcaaggca gagccaagac aatacccttg   2520
tatctgcgga tcatgtccag ccacctgtag actttgtgca agcgatgatg tctatgatgg   2580
aggcgatatc acagagagta agtaaggttg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
cctctcccta tgtgacacaa ggaggcgaaa tggcacttaa taaactttcg caaccagtgc   2880
```

-continued

```
cacatccatc tgaattgatt aaacccgcca ctgcatgcgg gcctgatata ggagtggaaa   2940
aggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
ggaatctgca ccgagttccc ccccgcagac ccaaggtcca actctccaag cggcaatcct   3180
ctctcgcttc ctcagcccca ctgaatggtc gcgtaaccgt aattaatcta gctacattta   3240
agattaagaa aaaatacggg tagaattgga gtgccccaat tgtgccaaga tggactcatc   3300
taggacaatt gggctgtact ttgattctgc ccattcttct agcaacctgt tagcatttcc   3360
gatcgtccta caaggcacag gagatgggaa gaagcaaatc gccccgcaat ataggatcca   3420
gcgccttgac ttgtggactg atagtaagga ggactcagta ttcatcacca cctatggatt   3480
catctttcaa gttgggaatg aagaagccac tgtcggcatg atcgatgata aacccaagcg   3540
cgagttactt tccgctgcga tgctctgcct aggaagcgtc ccaaataccg gagaccttat   3600
tgagctggca agggcctgtc tcactatgat agtcacatgc aagaagagtg caactaatac   3660
tgagagaatg gttttctcag tagtgcaggc accccaagtg ctgcaaagct gtagggttgt   3720
ggcaaacaaa tactcatcag tgaatgcagt caagcacgtg aaagcgccag agaagattcc   3780
cgggagtgga accctagaat acaaggtgaa ctttgtctcc ttgactgtgg taccgaagaa   3840
ggatgtctac aagatcccag ctgcagtatt gaaggtttct ggctcgagtc tgtacaatct   3900
tgcgctcaat gtcactatta atgtggaggt agacccgagg agtcctttgg ttaaatcttt   3960
gtctaagtct gacagcggat actatgctaa cctcttcttg catattggac ttatgaccac   4020
cgtagatagg aaggggaaga aagtgacatt tgacaagctg gaaaagaaaa taaggagcct   4080
tgatctatct gtcgggctca gtgatgtgct cgggccttcc gtgttggtaa aagcaagagg   4140
tgcacggact aagcttttgg cacctttctt ctctagcagt gggacagcct gctatcccat   4200
agcaaatgct tctcctcagg tggccaagat actctggagt caaaccgcgt gcctgcggag   4260
cgttaaaatc attatccaag caggtaccca acgcgctgtc gcagtgaccg ccgaccacga   4320
ggttacctct actaagctgg agaaggggca cacccttgcc aaatacaatc cttttaagaa   4380
ataagctgcg tctctgagat tgcgctccgc ccactcaccc agatcatcat gacacaaaaa   4440
actaatctgt cttgattatt tacagttagt ttacctgtct atcaagttag aaaaaaacacg   4500
ggtagaagat tctggatccc ggttggcgcc ctccaggtgc aagatgggct ccagaccttc   4560
taccaagaac ccagcaccta tgatgctgac tatccgggtt gcgctggtac tgagttgcat   4620
ctgtccggca aactccattg atggcaggcc tcttgcagct gcaggaattg tggttacagg   4680
agacaaagcc gtcaacatat acacctcatc ccagacagga tcaatcatag ttaagctcct   4740
cccgaatctg cccaaggata aggaggcatg tgcgaaagcc cccttggatg catacaacag   4800
gacattgacc actttgctca ccccccttgg tgactctatc cgtaggatac aagagtctgt   4860
gactacatct ggagggggga gacaggggcg ccttataggc gccattattg gcggtgtggc   4920
tcttggggtt gcaactgccg cacaaataac agcggccgca gctctgatac aagccaaaca   4980
aaatgctgcc aacatcctcc gacttaaaga gagcattgcc gcaaccaatg aggctgtgca   5040
tgaggtcact gacggattat cgcaactagc agtggcagtt gggaagatgc agcagtttgt   5100
taatgaccaa tttaataaaa cagctcagga attagactgc atcaaaattg cacagcaagt   5160
tggtgtagag ctcaacctgt acctaaccga attgactaca gtattcggac cacaaatcac   5220
ttcacctgct ttaaacaagc tgactattca ggcactttac aatctagctg gtggaaatat   5280
```

-continued

```
ggattactta ttgactaagt taggtgtagg gaacaatcaa ctcagctcat taatcggtag   5340
cggcttaatc accggtaacc ctattctata cgactcacag actcaactct tgggtataca   5400
ggtaactcta ccttcagtcg ggaacctaaa taatatgcgt gccacctact tggaaacctt   5460
atccgtaagc acaaccaggg gatttgcctc ggcacttgtc cccaaagtgg tgacacaggt   5520
cggttctgtg atagaagaac ttgacacctc atactgtata gaaactgact tagatttata   5580
ttgtacaaga atagtaacgt tccctatgtc ccctggtatt tattcctgct tgagcggcaa   5640
tacgtcggcc tgtatgtact caaagaccga aggcgcactt actacaccat acatgactat   5700
caaaggttca gtcatcgcca actgcaagat gacaacatgt agatgtgtaa accccccggg   5760
tatcatatcg caaaactatg gagaagccgt gtctctaata gataaacaat catgcaatgt   5820
tttatcctta ggcgggataa ctttaaggct cagtggggaa ttcgatgtaa cttatcagaa   5880
gaatatctca atacaagatt ctcaagtaat aataacaggc aatcttgata tctcaactga   5940
gcttgggaat gtcaacaact cgatcagtaa tgctttgaat aagttagagg aaagcaacag   6000
aaaactagac aaagtcaatg tcaaactgac tagcacatct gctctcatta cctatatcgt   6060
tttgactatc atatctcttg tttttggtat acttagcctg attctagcat gctacctaat   6120
gtacaagcaa aaggcgcaac aaaagacctt attatggctt gggaataata ctctagatca   6180
gatgagagcc actacaaaaa tgtgaacaca gatgaggaac gaaggtttcc ctaatagtaa   6240
tttgtgtgaa agttctggta gtctgtcagt tcagagagtt aagaaaaaac taccggttgt   6300
agatgaccaa aggacgatat acgggtagaa cggtaagaga ggccgcccct caattgcgag   6360
ccaggcttca caacctccgt tctaccgctt caccgacaac agtcctcaat catggaccgc   6420
gccgttagcc aagttgcgtt agagaatgat gaaagagagg caaaaaatac atggcgcttg   6480
atattccgga ttgcaatctt attcttaaca gtagtgacct tggctatatc tgtagcctcc   6540
cttttatata gcatgggggc tagcacacct agcgatcttg taggcatacc gactaggatt   6600
tccagggcag aagaaaagat tacatctaca cttggttcca atcaagatgt agtagatagg   6660
atatataagc aagtggccct tgagtctccg ttggcattgt taaatactga gaccacaatt   6720
atgaacgcaa taacatctct ctcttatcag attaatggag ctgcaaacaa cagtgggtgg   6780
ggggcaccta tccatgaccc agattatata ggggggatag gcaaagaact cattgtagat   6840
gatgctagtg atgtcacatc attctatccc tctgcatttc aagaacatct gaattttatc   6900
ccggcgccta ctacaggatc aggttgcact cgaataccct catttgacat gagtgctacc   6960
cattactgct acacccataa tgtaatattg tctggatgca gagatcactc acattcatat   7020
cagtatttag cacttggtgt gctccggaca tctgcaacag ggagggtatt cttttctact   7080
ctgcgttcca tcaacctgga cgacacccaa aatcggaagt cttgcagtgt gagtgcaact   7140
cccctgggtt gtgatatgct gtgctcgaaa gtcacggaga cagaggaaga agattataac   7200
tcagctgtcc ctacgcggat ggtacatggg aggttagggt tcgacggcca gtaccacgaa   7260
aaggacctag atgtcacaac attattcggg gactgggtgg ccaactaccc aggagtaggg   7320
ggtggatctt ttattgacag ccgcgtatgg ttctcagtct acggagggtt aaaacccaat   7380
tcacccagtg acactgtaca ggaagggaaa tatgtgatat acaagcgata caatgacaca   7440
tgcccagatg agcaagacta ccagattcga atggccaagt cttcgtataa gcctggacgg   7500
tttggtggga aacgcataca gcaggctatc ttatctatca aggtgtcaac atccttaggc   7560
gaagacccgg tactgactgt accgcccaac acagtcacac tcatgggggc cgaaggcaga   7620
```

-continued

```
attctcacag tagggacatc tcatttcttg tatcaacgag ggtcatcata cttctctccc   7680
gcgttattat atcctatgac agtcagcaac aaaacagcca ctcttcatag tccttataca   7740
ttcaatgcct tcactcggcc aggtagtatc ccttgccagg cttcagcaag atgccccaac   7800
tcgtgtgtta ctggagtcta tacagatcca tatcccctaa tcttctatag aaaccacacc   7860
ttgcgagggg tattcgggac aatgcttgat ggtgtacaag caagacttaa ccctgcgtct   7920
gcagtattcg atagcacatc ccgcagtcgc attactcgag tgagttcaag cagtaccaaa   7980
gcagcataca caacatcaac ttgttttaaa gtggtcaaga ctaataagac ctattgtctc   8040
agcattgctg aaatatctaa tactctcttc ggagaattca gaatcgtccc gttactagtt   8100
gagatcctca aagatgacgg ggttagagaa gccaggtctg gctagttgag tcaattataa   8160
aggagttgga aagatggcat tgtatcacct atcttctgcg acatcaagaa tcaaaccgaa   8220
tgccggcgcg tgctcgaatt ccatgttgcc agttgaccac aatcagccag tgctcatgcg   8280
atcagattaa gccttgtcat taatctcttg attaagaaaa aatgtaagtg gcaatgagat   8340
acaaggcaaa acagctcatg gtaaataata cgggtaggac atggcgagct ccggtcctga   8400
aagggcagag catcagatta tcctaccaga gccacacctg tcttcaccat tggtcaagca   8460
caaactactc tattactgga aattaactgg gctaccgctt cctgatgaat gtgacttcga   8520
ccacctcatt ctcagccgac aatggaaaaa aatacttgaa tcggcctctc ctgatactga   8580
gagaatgata aaactcggaa gggcagtaca ccaaactctt aaccacaatt ccagaataac   8640
cggagtgctc caccccaggt gtttagaaca actggctaat attgaggtcc cagattcaac   8700
caacaaattt cggaagattg agaagaagat ccaaattcac aacacgagat atggagaact   8760
gttcacaagg ctgtgtacgc atatagagaa gaaactgctg gggtcatctt ggtctaacaa   8820
tgtcccccgg tcagaggagt tcagcagcat tcgtacggat ccggcattct ggtttcactc   8880
aaaatggtcc acagccaagt ttgcatggct ccatataaaa cagatccaga ggcatctgat   8940
ggtggcagct aagacaaggt ctgcggccaa caaattggtg atgctaaccc ataaggtagg   9000
ccaagtcttt gtcactcctg aacttgtcgt tgtgacgcat acgaatgaga acaagttcac   9060
atgtcttacc caggaacttg tattgatgta tgcagatatg atggagggca gagatatggt   9120
caacataata tcaaccacgg cggtgcatct cagaagctta tcagagaaaa ttgatgacat   9180
tttgcggtta atagacgctc tggcaaaaga cttgggtaat caagtctacg atgttgtatc   9240
actaatggag ggatttgcat acggagctgt ccagctactc gagccgtcag gtacatttgc   9300
aggagatttc ttcgcattca acctgcagga gcttaaagac attctaattg gcctcctccc   9360
caatgatata gcagaatccg tgactcatgc aatcgctact gtattctctg gtttagaaca   9420
gaatcaagca gctgagatgt tgtgtctgtt gcgtctgtgg ggtcacccac tgcttgagtc   9480
ccgtattgca gcaaaggcag tcaggagcca aatgtgcgca ccgaaaatgg tagactttga   9540
tatgatcctt caggtactgt ctttcttcaa gggaacaatc atcaacgggt acagaaagaa   9600
gaatgcaggt gtgtggccgc gagtcaaagt ggatacaata tatgggaagg tcattgggca   9660
actacatgca gattcagcag agatttcaca cgatatcatg ttgagagagt ataagagttt   9720
atctgcactt gaatttgagc catgtataga atatgaccct gtcaccaacc tgagcatgtt   9780
cctaaaagac aaggcaatcg cacaccccaa cgataattgg cttgcctcgt ttaggcggaa   9840
ccttctctcc gaagaccaga agaaacatgt aaaagaagca acttcgacta atcgcctctt   9900
gatagagttt ttagagtcaa atgattttga tccatataaa gagatggaat atctgacgac   9960
ccttgagtac cttagagatg acaatgtggc agtatcatac tcgctcaagg agaaggaagt  10020
```

-continued

```
gaaagttaat ggacggatct tcgctaagct gacaaagaag ttaaggaact gtcaggtgat  10080
ggcggaaggg atcctagccg atcagattgc acctttcttt cagggaaatg gagtcattca  10140
ggatagcata tccttgacca agagtatgct agcgatgagt caactgtctt ttaacagcaa  10200
taagaaacgt atcactgact gtaaagaaag agtatcttca aaccgcaatc atgatccgaa  10260
aagcaagaac cgtcggagag ttgcaacctt cataacaact gacctgcaaa agtactgtct  10320
taattggaga tatcagacaa tcaaattgtt cgctcatgcc atcaatcagt tgatgggcct  10380
acctcacttc ttcgaatgga ttcacctaag actgatggac actacgatgt tcgtaggaga  10440
ccctttcaat cctccaagtg accctactga ctgtgacctc tcaagagtcc ctaatgatga  10500
catatatatt gtcagtgcca gagggggtat cgaaggatta tgccagaagc tatggacaat  10560
gatctcaatt gctgcaatcc aacttgctgc agctagatcg cattgtcgtg ttgcctgtat  10620
ggtacagggt gataatcaag taatagcagt aacgagagag gtaagatcag acgactctcc  10680
ggagatggtg ttgacacagt tgcatcaagc cagtgataat ttcttcaagg aattaattca  10740
tgtcaatcat ttgattggcc ataatttgaa ggatcgtgaa accatcaggt cagacacatt  10800
cttcatatac agcaaacgaa tcttcaaaga tggagcaatc ctcagtcaag tcctcaaaaa  10860
ttcatctaaa ttagtgctag tgtcaggtga tctcagtgaa aacaccgtaa tgtcctgtgc  10920
caacattgcc tctactgtag cacggctatg cgagaacggg cttcccaaag acttctgtta  10980
ctatttaaac tatataatga gttgtgtgca gacatacttt gactctgagt tctccatcac  11040
caacaattcg caccccgatc ttaatcagtc gtggattgag gacatctctt ttgtgcactc  11100
atatgttctg actcctgccc aattaggggg actgagtaac cttcaatact caaggctcta  11160
cactagaaat atcggtgacc cggggactac tgcttttgca gagatcaagc gactagaagc  11220
agtgggatta ctgagtccta acattatgac taatatctta actaggccgc ctgggaatgg  11280
agattgggcc agtctgtgca acgacccata ctctttcaat tttgagactg ttgcaagccc  11340
aaatattgtt cttaagaaac atacgcaaag agtcctattt gaaacttgtt caaatccctt  11400
attgtctgga gtgcacacag aggataatga ggcagaagag aaggcattgg ctgaattctt  11460
gcttaatcaa gaggtgattc atccccgcgt tgcgcatgcc atcatggagg caagctctgt  11520
aggtaggaga aagcaaattc aagggcttgt tgacacaaca aacaccgtaa ttaagattgc  11580
gcttactagg aggccattag gcatcaagag gctgatgcgg atagtcaatt attctagcat  11640
gcatgcaatg ctgtttagag acgatgtttt ttcctccagt agatccaacc acccettagt  11700
ctcttctaat atgtgttctc tgacactggc agactatgca cggaatagaa gctggtcacc  11760
tttgacggga ggcaggaaaa tactgggtgt atctaatcct gatacgatag aactcgtaga  11820
gggtgagatt cttagtgtaa gcggagggtg tacaagatgt gacagcggag atgaacaatt  11880
tacttggttc catcttccaa gcaatataga attgaccgat gacaccagca agaatcctcc  11940
gatgagggta ccatatctcg ggtcaaagac acaggagagg agagctgcct cacttgcaaa  12000
aatagctcat atgtcgccac atgtaaaggc tgccctaagg gcatcatccg tgttgatctg  12060
ggcttatggg gataatgaag taaattggac tgctgctctt acgattgcaa aatctcggtg  12120
taatgtaaac ttagagtatc ttcggttact gtccccttta cccacggctg ggaatcttca  12180
acatagacta gatgatggta taactcagat gacattcacc cctgcatctc tctacaggtg  12240
tcaccttaca ttcacatatc caatgattct caaaggctgt tcactgaaga aggagtcaaa  12300
gaggggaatg tggtttacca acagagtcat gctcttgggt ttatctctaa tcgaatcgat  12360
```

-continued

```
ctttccaatg acaacaacca ggacatatga tgagatcaca ctgcacctac atagtaaatt  12420
tagttgctgt atcagagaag cacctgttgc ggttcctttc gagctacttg gggtggtacc  12480
ggaactgagg acagtgacct caaataagtt tatgtatgat cctagccctg tatcggaggg  12540
agactttgcg agacttgact tagctatctt caagagttat gagcttaatc tggagtcata  12600
tcccacgata gagctaatga acattctttc aatatccagc gggaagttga ttggccagtc  12660
tgtggtttct tatgatgaag atacctccat aaagaatgac gccataatag tgtatgacaa  12720
tacccgaaat tggatcagtg aagctcagaa ttcagatgtg gtccgcctat ttgaatatgc  12780
agcacttgaa gtgctcctcg actgttctta ccaactctat tacctgagag taagaggcct  12840
agacaatatt gtcttatata tgggtgattt atacaagaat atgccaggaa ttctactttc  12900
caacattgca gctacaatat ctcatcccgt cattcattca aggttacatg cagtgggcct  12960
ggtcaaccat gacggatcac accaacttgc agatacggat tttatcgaaa tgtctgcaaa  13020
actattagta tcttgcaccc gacgtgtgat ctccggctta tattcaggaa ataagtatga  13080
tctgctgttc ccatctgtct tagatgataa cctgaatgag aagatgcttc agctgatatc  13140
ccggttatgc tgtctgtaca cggtactctt tgctacaaca agagaaatcc cgaaaataag  13200
aggcttaact gcagaagaga aatgttcaat actcactgag tatttactgt cggatgctgt  13260
gaaaccatta cttagccccg atcaagtgag ctctatcatg tctcctaaca taattacatt  13320
cccagctaat ctgtactaca tgtctcggaa gagcctcaat ttgatcaggg aaagggagga  13380
cagggatact atcctggcgt tgttgttccc ccaagagcca ttattagagt tcccttctgt  13440
gcaagatatt ggtgctcgag tgaaagatcc attcacccga caacctgcgg catttttgca  13500
agagttagat ttgagtgctc cagcaaggta tgacgcattc acacttagtc agattcatcc  13560
tgaactcaca tctccaaatc cggaggaaga ctacttagta cgatacttgt tcagagggat  13620
agggactgca tcttcctctt ggtataaggc atctcatctc ctttctgtac ccgaggtaag  13680
atgtgcaaga cacgggaact ccttatactt agctgaaggg agcggagcca tcatgagtct  13740
tctcgaactg catgtaccac atgaaactat ctattacaat acgctctttt caaatgagat  13800
gaaccccccg caacgacatt tcgggccgac ccccaactcag tttttgaatt cggttgttta  13860
taggaatcta caggcggagg taacatgcaa agatggattt gtccaagagt tccgtccatt  13920
atggagagaa aatacagagg aaagtgacct gacctcagat aaagcagtgg ggtatattac  13980
atctgcagtg ccctacagat ctgtatcatt gctgcattgt gacattgaaa ttcctccagg  14040
gtccaatcaa agcttactag atcaactagc tatcaattta tctctgattg ccatgcattc  14100
tgtaagggag ggcggggtag taatcatcaa agtgttgtat gcaatgggat actactttca  14160
tctactcatg aacttgtttg ctccgtgttc cacaaaagga tatattctct ctaatggtta  14220
tgcatgtcga ggagatatgg agtgttacct ggtatttgtc atgggttacc tgggcgggcc  14280
tacatttgta catgaggtgg tgaggatggc aaaaactctg gtgcagcggc acggtacgct  14340
cttgtctaaa tcagatgaga tcacactgac caggttattc acctcacagc ggcagcgtgt  14400
gacagacatc ctatccagtc ctttaccaag attaataaag tacttgagga agaatattga  14460
cactgcgctg attgaagccg gggacagcc cgtccgtcca ttctgtgcgg agagtctggt  14520
gagcacgcta gcgaacataa ctcagataac ccagattatc gctagtcaca ttgacacagt  14580
tatccggtct gtgatatata tggaagctga gggtgatctc gctgacacag tatttctatt  14640
taccccttac aatctctcta ctgacgggaa aaagaggaca tcacttatac agtgcacgag  14700
acagatccta gaggttacaa tactaggtct tagagtcgaa aatctcaata aaataggcga  14760
```

-continued

```
tataatcagc ctagtgctta aaggcatgat ctccatggag gaccttatcc cactaaggac  14820

atacttgaag catagtacct gccctaaata tttgaaggct gtcctaggta ttaccaaact  14880

caaagaaatg tttacagaca cttctgtatt gtacttgact cgtgctcaac aaaaattcta  14940

catgaaaact ataggcaatg cagtcaaagg atattacagt aactgtgact cttaacgaaa  15000

atcacatatt aataggctcc ttttttggcc aattgtattc ttgttgattt aatcatatta  15060

tgttagaaaa aagttgaacc ctgactcctt aggactcgaa ttcgaactca aataaatgtc  15120

ttaaaaaaag gttgcgcaca attattcttg agtgtagtct cgtcattcac caaatctttg  15180

tttggt                                                             15186
```

```
<210> SEQ ID NO 4
<211> LENGTH: 1611
<212> TYPE: DNA
<213> ORGANISM: infectious bronchitis virus (IBV)

<400> SEQUENCE: 4

atgttggtaa cacctctttt actagtgact cttttgtgtg cactatgtag tgctgctttg    60

tatgacagta gttcttacgt gtactactac caaagtgcct tcagaccacc tgatggttgg   120

catttacatg gggtgcgta tgcggttgtt aatatttcta gtgaatctaa taatgcaggc   180

tcttcatctg ggtgtactgt tggtattatt catggtggtc gtgttgttaa tgcttcttct   240

atagctatga cggcaccgtc atcaggtatg gcttggtcta gcagtcagtt ttgtactgca   300

tactgtaact tttcagatac tacagtgttt gttacacatt gttacaaaca tgttgggtgt   360

cctataactg gcatgcttca acagcattct atacgtgttt ctgctatgaa aaatggccag   420

ctttttata atttaacagt tagtgtagct aagtacccta cttttaaatc atttcagtgt   480

gttaataatt taacatccgt atatttaaat ggtgatcttg tttacacctc taatgagacc   540

acagatgtta catctgcagg tgtttatttt aaagctggtg gacctataac ttataaagtt   600

atgagagaag ttagagccct ggcttatttt gttaatggta ctgcacaaga tgttattttg   660

tgtgatgggt cacctagagg cttgttagca tgccagtata atactggcaa tttttcagat   720

ggcttttatc cttttactaa tagtagttta gttaagcaga agtttattgt ctatcgtgaa   780

aatagtgtta atactacttt tacgttacac aatttcactt ttcataatga gactggcgcc   840

aacccaaatc ctagtggtgt ccagaatatt caaacttacc aaacacaaac agctcagagt   900

ggttattata attttaattt ttcctttctg agtagttttg tttataagga gtctaatttt   960

atgtatggat cttatcaccc aagttgtaat tttagactag aaactattaa taatggtttg  1020

tggtttaatt cactttcagt ttcaattgct tacggtcctc ttcaaggtgg ttgcaagcaa  1080

tctgtcttta gtggtagagc aacctgttgt tatgcttact catatggagg tcctttgctg  1140

tgtaaaggtg tttattcagg tgagttagat cataattttg aatgtggact gttagtttat  1200

gttactaaga gcggtggctc tcgtatacaa acagccactg aaccgccagt tataactcaa  1260

cacaattata ataatattac tttaaatact tgtgttgatt ataatatata tggcagaact  1320

ggccaaggtt ttattactaa tgtaaccgac tcagctgtta gttataatta tctagcagac  1380

gcaggtttgg ctattttaga tacatctggt tccatagaca tctttgtcgt acaaagtgaa  1440

tatggtctta attattataa ggttaaccct tgcgaagatg tcaaccagca gtttgtagtt  1500

tctggtggta aattagtagg tattcttact tcacgtaatg agactggttc ccagcttctt  1560

gagaatcagt tttacatcaa aatcactaat ggaacacgtc gttttagacg t            1611
```

-continued

<210> SEQ ID NO 5
<211> LENGTH: 960
<212> TYPE: DNA
<213> ORGANISM: infectious laryngotracheitis virus (ILTV)

<400> SEQUENCE: 5
ggaggggaga gagacaactt cagctcgaag tctgaagaga catcatgagc ggcttcagta 60
acataggatc gattgccacc gtttccctag tatgctcgct tttgtgcgca tctgtattag 120
gggcgccggt actggacggg ctcgagtcga gccctttccc gttcgggggc aaaattatag 180
cccaggcgtg caaccgcacc acgattgagg tgacggtccc gtggagcgac tactctggtc 240
gcaccgaagg agtgtcagtc gaggtgaaat ggttctacgg gaatagtaat cccgaaagct 300
tcgtgttcgg ggtggatagc gaaacgggca gtggacacga ggacctgtct acgtgctggg 360
ctctaatcca taatctgaac gcgtctgtgt gcagggcgtc tgacgccggg atacctgatt 420
tcgacaagca gtgcgaaaaa gtgcagagaa gactgcgctc cggggtggaa cttggtagtt 480
acgtgtctgg caatggatcc ctggtgctgt acccagggat gtacgatgcc ggcatctacg 540
cctaccagct ctcagtgggt gggaagggat ataccgggtc tgtttatcta gacgtcggac 600
caaaccccgg atgccacgac cagtatgggt acacctatta cagcctggcc gacgaggcgt 660
cagacttatc atcttatgac gtagcctcgc ccgaactcga cggtcctatg gaggaagatt 720
attccaattg tctagacatg cccccgctac gcccatggac aaccgtttgt tcgcatgacg 780
tcgaggagca ggaaaacgcc acggacgagc tttacctatg ggacgaggaa tgcgccggtc 840
cgctggacga gtacgtcgac gaaaggtcag agacgatgcc caggatggtt gtcttttcac 900
cgccctctac gctccagcag tagccacccg agagtgtttt ttgtgagcgc ccacgcaaca 960

<210> SEQ ID NO 6
<211> LENGTH: 810
<212> TYPE: DNA
<213> ORGANISM: avian encephalomyelitis virus (AEV)

<400> SEQUENCE: 6
gggaaagagg atgaaggagg atttttcagt gtgcctgaag tggagcaaca tgttgttgag 60
gataaggaac cacagggacc tttgcacgtg acaccttttg gcgctgttaa agctatggag 120
gacccccaat tggccaggaa aacacctggc acattccctg aattagctcc tggtaaacct 180
cgacatacag tggaccacat ggatctgtat aagttcatgg ggcgtgccca ttacttgtgg 240
ggacatgaat tcaccaaaac tgacatgcag tacacattcc agataccatt aagtcccatt 300
aaagagggtt ttgtgacggg tacacttagg tggtttttaa gtcttttcca actgtatcgt 360
ggttctctcg acattaccat gacatttgca ggaaaaacta atgtggatgg cattgtgtac 420
tttgtgcctg agggtgttgc gatagagact gagagggagg agcagacccc tttgctcaca 480
ttgaactata aaacatcggt aggtgccatt aggtttaata ctggacaaac tacgaatgtc 540
cagtttagga tccctttcta cacgccactg gaacacatcg caacccattc taaaaatgcg 600
atggattcag tcttgggggc aatcacaacc cagatcacta actatagtgc tcaggatgag 660
tatttgcagg ttacctacta catcagtttc aatgaagatt cacagttttc tgttcccaga 720
gcggtgccag tggtcagctc attcactgac acatctagca aaacagtgat gaatacatat 780
tggcttgatg atgacgagtt ggtagaagag 810

<210> SEQ ID NO 7

-continued

<211> LENGTH: 726
<212> TYPE: DNA
<213> ORGANISM: avian encephalomyelitis virus (AEV)

<400> SEQUENCE: 7
atgagcaaac tattttctac tgtaggcagg actgttgatg aggttttgtc tgtgctcaat 60
gatgaggata ctgaatctta tgctggccct gatcgcactg cagtagttgg cggaggattt 120
ctgacaacgg tagaccagag ttcagttagc acggctacaa tgggaagttt acaagatgta 180
cagtacagga ctgcagtcga tattcctggt tctagagtga cacaaggtga gaggttcttc 240
cttatcgatc agcgtgagtg gaactcaaca cagagtgaat ggcagttatt gggcaagatt 300
gacatagtaa aagagctgct tgatcagtcg tatgctgttg atggcctttt gaagtaccat 360
tcttatgcaa ggtttggctt ggatgtcatt gttcagatta atccaacatc attccaggca 420
gggggcctca tagcagctct cgtaccttat gaccaggttg acattgaatc aattgttgcc 480
atgaccactt attgccatgg caaggttaat tgcaacataa actacgttgt aaggatgaag 540
gtgccatata tatacagtcg aggttgttac aaccttagga actcagcata ctccatttgg 600
atgcttgtga taagagtgtg gtcacggctg cagttgggat ctggcacttc aacacagatt 660
actatcacca ccttggctag gtttgtggat ttggaactgc atggacttag ccctttggtc 720
gcacag 726

<210> SEQ ID NO 8
<211> LENGTH: 735
<212> TYPE: DNA
<213> ORGANISM: avian encephalomyelitis virus (AEV)

<400> SEQUENCE: 8
atgatgcgca acgaatttcg actgtcgtca tctagcaaca ttgtcaattt ggctaattat 60
gacgatgcaa gagccaaagt gtctctagcg ctgggacaag aagagttttc cagagactcg 120
tcaagtaccg ggggggaatt ggtgcatcat tttcacagt ggacgtccat tccgtgcctt 180
gccttcactt ttacattccc cggcacggta gggccaggca ctcacatctg gtcaaccacg 240
gtggaccctt tttcctgtaa cttgagggcg tctagcactg tgcaccccac taacttgagc 300
tcgattgcgg gtatgttctg tttttggaga ggtgacattg tatttgagtt tcaagtcttt 360
tgcaccaagt atcattccgg caggttgatg tttgtgtatg tgcctggcga tgaaaacaca 420
aaaatcagca ccttaactgc aaaacaagca tctactggtc ttactgctgt ttttgatatc 480
aatggtgtaa attcaacact ggtgtttaga tgccctttca tctctgacac accttacagg 540
gtgaatccaa cgactcataa gtccctctgg ccttatgcaa ctggcaagct tgtgtgctat 600
gtctacaata tactgaacgc acctgccagt gtatcaccaa ccctgcccat taatgtgtac 660
aaaagtgctg cggatctgga gttgtatgca cctgtttatg ggtttctcc caccaacacc 720 tcaatttttg ttcaa 735

<210> SEQ ID NO 9
<211> LENGTH: 1500
<212> TYPE: DNA
<213> ORGANISM: avian parainfluenza virus (APV)

<400> SEQUENCE: 9
ggggggtgtg catggtaggg tggggaaggt agccaattcc tgcccattgg gccgaccgta 60
ccaagagaag tcaacagaag tatagatgca gggcgacatg gagggtagcc gtgataacct 120
cacagtagat gatgaattaa agacaacatg gaggttagct tatagagttg tatccctcct 180

-continued

```
attgatggtg agtgccttga taatctctat agtaatcctg acgagagata acagccaaag    240

cataatcacg gcgatcaacc agtcgtatga cgcagactca aagtggcaaa cagggataga    300

agggaaaatc acctcaatca tgactgatac gctcgatacc aggaatgcag ctcttctcca    360

cattccactc cagctcaata cacttgaggc aaacctgttg tccgccctcg gaggttacac    420

gggaattggc cccggagatc tagagcactg tcgttatccg gttcatgact ccgcttacct    480

gcatggagtc aatcgattac tcatcaatca aacagctgac tacacagcag aaggccccct    540

ggatcatgtg aacttcattc cggcaccagt tacgactact ggatgcacaa ggatcccatc    600

cttttctgta tcatcatcca tttggtgcta tacacacaat gtgattgaaa caggttgcaa    660

tgaccactca ggtagtaatc aatatatcag tatgggggtg attaagaggg ctggcaacgg    720

cttaccttac ttctcaacag tcgtgagtaa gtatctgacc gatgggttga atagaaaaag    780

ctgttccgta gctgcgggat ccgggcattg ttacctcctt tgtagcctag tgtcagagcc    840

cgaacctgat gactatgtgt caccagatcc cacaccgatg aggttagggg tgctaacaag    900

ggatgggtct tacactgaac aggtggtacc cgaaagaata tttaagaaca tatggagcgc    960

aaactaccct ggggtagggt caggtgctat agcaggaaat aaggtgttat tcccatttta   1020

cggcggagtg aagaatggat caacccctga ggtgatgaat aggggaagat attactacat   1080

ccaggatcca aatgactatt gccctgaccc gctgcaagat cagatcttaa gggcagaaca   1140

atcgtattat cctactcgat ttggtaggag gatggtaatg cagggagtcc taacatgtcc   1200

agtatccaac aattcaacaa tagccagcca atgccaatct tactatttca acaactcatt   1260

aggattcatc ggggcggaat ctaggatcta ttacctcaat ggtaacattt acctttatca   1320

aagaagctcg agctggtggc ctcacccccca aatttaccta cttgattcca ggattgcaag   1380

tccgggtacg cagaacattg actcaggcgt taacctcaag atgttaaatg ttactgtcat   1440

tacacgacca tcatctggct tttgtaatag tcagtcaaga tgccctaatg actgcttatt   1500
```

<210> SEQ ID NO 10
<211> LENGTH: 1440
<212> TYPE: DNA
<213> ORGANISM: hemorrhagic enteritis virus (HEV)

<400> SEQUENCE: 10

```
gaaatgttaa tgttagacca tactgaccaa ttcctggttc attttagatg gaatcttcga     60

acactgccac tagaattttt gctccaacgg aagggagaaa cagtataatt tacagcaact    120

tgcctcctgt tcaagataca accaaaatat tttatataga taacaaggcc attgatatag    180

agtcatataa tcaagagaaa gatcattcta attattatac taatataatt caaacacaga    240

acatttcaac tattgattca agtatacagc aaattcagtt agatgaaagg tctagatggg    300

gaggagaact acatacaagc ttagtaacat ctgttatgaa ttgtactaaa cattttaatt    360

cagataggtg tttagtgaaa attcagacta ttaagagtcc acctacattt gaatggaaag    420

aattgaaaat acctgaggga aactatgttt taaatgagtt tattgattta ttaaatgaag    480

gtattacttc tttatacctt cagtatggca ggcaacaggg tgtacttgaa gaagacatag    540

gaataaaatt tgatactcgc aattttgaaa ttggtaaaga tccaactact aatcttgtta    600

ctcctggtaa atacttgttt aagggttatc atgctgatat aatacttctt cctggttggg    660

ctattgattt ttctttttct agattgggta acattttagg tattagaaaa cgtgagactt    720

ataaagctgg ctttttgatt gaatatgatg acttgacaaa tggtaatatt ccaccactgt    780
```

-continued

```
tggatgttgc taactataag tctacaagtc aagctaaacc attattacag gatccatctg    840

gcagatctta ccacgttatg gatagtgatt ctaacagacc tgtgactgca tataggtctt    900

ttgttttgtc atataacaat gaaggtgctg caaaattaaa gtttttgatg tgtatgagtg    960

atataacggg gggtctcaat cagctgtatt ggtgtttgcc tgattcttat aaaccgccag   1020

tatcttttaa gcaagaaacg caagtagata aactgcctgt tgttggtatg caacttttttt  1080

tcctttttgt ttgtaaatct gtgtattctg gtgctgctgt ttacacacag ttaattgaac   1140

agcagactaa tttgacacaa atttttaaca gatttcatga taatgaaatt ttaaaacaag   1200

ctccatatgt gaatcaagtt ttattggctg aaaatgtgcc cataaatgtt aatcagggaa   1260

caataccaat attttcaact cttccaggag tacagagagt ggttgtggaa gacgatagga   1320

gaagaactgt accctacgtt accaagtcac ttgctacagt atatccgaag gttttgtcta   1380

gcaaaacttt gcaataatgc attctgttgt ttattctcca ggggacagta gaggatgggg   1440
```

<210> SEQ ID NO 11
<211> LENGTH: 2995
<212> TYPE: DNA
<213> ORGANISM: fowlpox virus (FPV)

<400> SEQUENCE: 11

```
ctcttaattc gtttcaaaaa tgggaaatat ttttaagcct attccaaagg ccgattatca     60

gattgtggaa acagtaccac aaagcttaac agctattaat tctactaatc tttctactta    120

tgaatgtttt aaacgtttaa tagatctagc aaaaaaagag atctacatag ctacgttttg    180

ttgtaaccta agtactaatc ctgagggtac tgacatacta aacagattaa tcgatgtttc    240

gagtaaagtt tctgtatata ttttagtaga tgagagcagt cctcataaag attatgaaaa    300

gattaagtct tcccatatta gttatattaa agtagatata ggtgtgctta ataatgaatc    360

agtaggaaac ttgttaggta atttctgggt agtggataag cttcactttt atataggtag    420

tgcgtctctt atgggaaatg cgctaacaac tattaaaaat atgggcatat attccgaaaa    480

taattcttta gcaatggatt tatatttcag atcgttggac tataaaatta taagcaagaa    540

aaaatgttta ttctttacca gaatggccac aaagtaccat ttcttcaaaa accataacgg    600

tatattcttt tcagattctc cagaacatat ggtaggtaga aaaagaactt ttgacttgga    660

ttgtgttatt cattatatag acgcggcgaa gtctactata gatctagcga tagtatctct    720

tcttcctaca aagagaacaa aagattctat cgtctattgg cctataataa aagatgcatt    780

aatacgggcc gtattagaac gaggtgtcaa actacgagtg ctattaggat tttggaaaaa    840

aacggatgtt atatcaaaag catctataaa aagccttaac gaactaggag ttgaccatat    900

agatatctct actaaagtat ttaggtttcc cgttaattct aaagtagatg atattaataa    960

ttctaaaatg atgattatag atggaaggta tgctcatgtt atgactgcta acctagacgg   1020

gtctcatttt aatcaccatg cttttgttag ctttaactgt atggatcaac aatttacaaa   1080

gaaaatagct gaagtgtttg aaagggactg gatatctcct tacgcaaaag aaatagatat   1140

gtctcaaata tagtatatat gataaaaaga tcctaataaa taaatatagc atggcactaa   1200

tagaacagtt acaatcttct gaacaatcaa tactttcacc gtttagatat tatggtttta   1260

aagattttca taatgtaatt tttaccacaa tagatgacga aacattaata gtaattacag   1320

tcaacaatgt accattagta actaggttaa taacgtttga aaaaataaca tttttttagat  1380

cgtttaatag tacttgtatt ataacttcca acaataattc ggatattgat acagatactt   1440
```

-continued

```
attttatacc aaattcgtta tcactactag atattttgaa gaaaagagca tatgatgtag   1500

aactaagaga tctatcattt gctataatgt cggaaatgaa taacgatgaa ttgagaaata   1560

gtgatattgt atctctaaac aaatggctac ataagcataa tttactagac tacaaattag   1620

tactaataag tgatatcgat agaagatata aattatacaa taaaaaaaat acaataattg   1680

atgttatatc cgtaaatggt agaaattata atatatgggt taaagatgtt atagaatatt   1740

attcaccgga atacttaaga tggtctatag atattaaaag agccacagaa agtaataact   1800

ggttaccgta tagccagtct ataaaccctt tgaatgaaaa tatatacgct tttgaattta   1860

tagctacttt agaaagatcc aatgagcgct taaatatcgg agcgatattc ctgtatccgg   1920

atataataat tacaggtaga aacaacgaag atataataga aaagttttta gatcagttag   1980

aagaagtaat atataaaaaa aattctgata gtattgtttt aacaggttat catctaacat   2040

ttttagagaa tactatttta gagagatata tcagtaagta taaagactgg atttttacat   2100

gtaatcgtct agtacattgt aaaaccggca ctgaagtatt cttatttgat gccgctatat   2160

tttttccatc ctctaataag aaaggatatg taaaacattg gacaggtaaa aaattaaatt   2220

ttaaaaactt tttccaaaaa gatagtcagc tagaaaaata cataaataat aacagtgtag   2280

cagaacgtat atattattta cagtcttctt tacacaagca tatatcctgt ctaatagaaa   2340

ttttcgagtt aaatggattt gattttaatt tttctgggtt gttagatata cttattttca   2400

gtattcgtgt taagaataat aatggtaatt actattaccc taaacattct tcagctgtga   2460

atttgatgtt gtcatctatt tacacggact attatgctat tgatgatata gataaagata   2520

gtaagaaact tgtttttaac tctatttttc ctttaataat ggaaggatat taccctgaag   2580

gaaaacctta ttatacgaaa acacccaaag aagggtattt gtcaatatgt ttatgtgatg   2640

tagaaatatc taatgatata aagaatccta tattgtattg taaagaaaac aagtcagcta   2700

ggaagtttac aggagtattc acatctgtag atatagatac cgctgtaaaa ctaagaggat   2760

ataaaattaa aatattagaa tgtattgaat ggcctaataa aataaaatta ttcgacaata   2820

tatgttatct gaataaatta tttatagaac atcaggatta cacacacgat gaaaaatctt   2880

tacaaggcta tctttttttct tatttactta aaggcaacgt taccgaagat gttttagcta   2940

tgaaaagttg tagaaataat ctttctataa tatcatttat aataagttac tgcag         2995
```

<210> SEQ ID NO 12
<211> LENGTH: 35
<212> TYPE: DNA
<213> ORGANISM: artificial sequence
<220> FEATURE:
<223> OTHER INFORMATION: PCR primer, IBS1F'

<400> SEQUENCE: 12

```
cgggatccgc cgccgccatg ttggtaacac ctctt                                 35
```

<210> SEQ ID NO 13
<211> LENGTH: 29
<212> TYPE: DNA
<213> ORGANISM: artificial sequence
<220> FEATURE:
<223> OTHER INFORMATION: PCR primer, IBS1R'

<400> SEQUENCE: 13

```
cggaattctt aacgtctaaa acgacgtgt                                        29
```

<210> SEQ ID NO 14
<211> LENGTH: 38

-continued

```
<212> TYPE: DNA
<213> ORGANISM: artificial sequence
<220> FEATURE:
<223> OTHER INFORMATION: PCR primer, NDF F'

<400> SEQUENCE: 14

cgggatccgc cgccgccatg ggctccagac cttctacc                              38


<210> SEQ ID NO 15
<211> LENGTH: 34
<212> TYPE: DNA
<213> ORGANISM: artificial sequence
<220> FEATURE:
<223> OTHER INFORMATION: PCR primer, NDF R'

<400> SEQUENCE: 15

ccgctcgagt tacatttttg tagtggctct catt                                  34


<210> SEQ ID NO 16
<211> LENGTH: 39
<212> TYPE: DNA
<213> ORGANISM: artificial sequence
<220> FEATURE:
<223> OTHER INFORMATION: PCR primer, NDHN F'

<400> SEQUENCE: 16

cgggatccgc cgccgccatg gaccgcgccg ttaggcaag                             39


<210> SEQ ID NO 17
<211> LENGTH: 29
<212> TYPE: DNA
<213> ORGANISM: artificial sequence
<220> FEATURE:
<223> OTHER INFORMATION: PCR primer, NDHN R'

<400> SEQUENCE: 17

gctctagatt actcaactag ccagacctg                                        29


<210> SEQ ID NO 18
<211> LENGTH: 35
<212> TYPE: DNA
<213> ORGANISM: artificial sequence
<220> FEATURE:
<223> OTHER INFORMATION: PCR primer, IBDVP2F'

<400> SEQUENCE: 18

cgggatccgc cgccgccatg acaaacctgc aagat                                 35


<210> SEQ ID NO 19
<211> LENGTH: 29
<212> TYPE: DNA
<213> ORGANISM: artificial sequence
<220> FEATURE:
<223> OTHER INFORMATION: PCR primer, IBDVP2R'

<400> SEQUENCE: 19

cggaattctt accttatggc ccggattat                                        29
```

VACCINE ACCELERATOR FACTOR (VAF) FOR IMPROVEMENT OF VACCINATIONS IN POULTRY

RELATED APPLICATION

The present application is a continuation-in-part (CIP) of U.S. patent application Ser. No. 10/377,718 filed on Mar. 4, 2003, which in turn claims the benefit of the filing date of U.S. provisional application No. 60/362,547, filed on Mar. 8, 2002, which are herein incorporated by reference.

FIELD OF THE INVENTION

The present invention relates to a vaccine accelerator factor (VAF) which is an in ovo nucleotides-immuno-stimulant containing one or more DNA constructs, each having a DNA molecule and a vector. Each of the DNA molecule contains one or more genes or gene fragments, each encoding an antigenic peptide of an avian virus. The VAF is preferably administered to the amniotic fluid of an egg, which has been fertilized for about 17–19 days. The VAF can be co-administered with a viral vaccine containing one or more attenuated or inactive avian viruses or a recombinant DNA vaccine. Alternatively, the VAF can be injected into egg prior to the administration of the viral vaccine. In that case, the viral vaccine is preferably administered at hatch or post-hatch. The VAF stimulates and accelerate a protective immune response of a viral vaccine against the avian virus of which the DNA molecule of the VAF contains a gene or a fragment thereof.

BACKGROUND OF THE INVENTION

Routine vaccinations used in veterinary practice have had a highly beneficial impact on the health and welfare of livestock and companion animals. Poultry vaccines can be administered via different routes and by various methods. For example, a post-hatch spray vaccination method has been widely used. This method can mass-immunize day old chicks through aerosol spray. Also, live or attenuated vaccines can be administered to poultry through traditional method, i.e., by subcutaneous injection to chicks, rearing stock and breeders. Furthermore, poultry vaccines can be delivered via eye drops and/or intranasal routes during brooding of chicks. Finally, and most prevalently, vaccines can be administered to poultry via drinking water. This vaccination method has the advantage of low cost, but its effectiveness, particularly against some infections, is limited due to less control of vaccination.

Most recently, some poultry vaccines have been administered to eggs through an in ovo injection method. A patented EMBREX INOVOJECT® system has been used to facilitate this kind of injection. The first in-ovo vaccination machine for use on chicken hatching eggs was developed by Embrex, Inc., of Raleigh, N.C. in the late 1980s. (See U.S. Pat. Nos. 5,056,464 and 5,699,751).

This in-ovo machine is currently used in about 80% of the U.S. broiler hatcheries, primarily for administering Marek's disease (MD) vaccines. The popularity of this machine, which has proven to be safe and effective in vaccination of chicks against MD, is also being used increasingly to administer infectious bursal disease (IBD) and Newcastle disease (ND) vaccines.

In ovo vaccination of virus-containing vaccines was extensively described by Sharma et al. (U.S. Pat. No. 4,458,630). In particular, it teaches that live Marek's disease virus can be injected into amniotic fluid within the egg, whereafter the embryo is infected and the vaccine virus replicates to a high titer which induces the formation of protective antibodies in the treated embryo. (See Sharma (1985), *Avian Diseases* 29, 1155, 1167–68).

It is well-known in the worldwide poultry business that certain viral diseases, such as Marek's disease virus (MDV), infectious bursal disease virus (IBDV), Newcastle disease virus (NDV), infectious bronchitis virus (IBV), infectious laryngotracheitis virus (ILTV), avian encephalomyelitis (AEV), chick anemia virus (CAV), Fowlpox virus (FPV), avian influenza virus (AIV), reovirus, avian leukosis virus (ALV), reticuloendotheliosis virus (REV), avian adenovirus and hemorrhagic enteritis virus (HEV), may cause major outbreak and result in significant economic losses in the commercial poultry industry. Among them, MDV, IBDV, NDV and IBV, are particularly important due to their virulent nature.

Marek's Disease (MD) is a malignant, lymphoproliferative disorder disease that occurs naturally in chickens. The disease is caused by a herpesvirus: Marek's Disease Virus (MDV). MD is ubiquitous, occurring in poultry-producing countries throughout the world. Chickens raised under intensive production systems will inevitably suffer losses from MD. The symptoms of MD appear widely in the nerves, genital organs, internal organs, eyes and skin of the infected birds, causing motor trouble (due to paralysis when the nerves have been affected), functional trouble of the internal organs (due to tumors), and chronic undernourishment (if the internal organs are attacked by the virus). MD affects chickens from about 6 weeks of age, occurring most frequently between ages of 12 and 24 weeks.

At of this time, there are no methods of treating MD. The control of the disease is based primarily on management methods such as insolating growing chickens from sources of infection, the use of genetically resistant stock, and vaccination. However, management procedures are normally not cost-effective and the progress has been disappointing with respect to the selection of poultry stock with increased genetically controlled resistance. Nowadays, control of MD is almost entirely based on vaccination.

Infectious bursal disease virus (IBDV) is responsible for a highly contagious immunosuppressive disease in young chickens which causes significant losses to the poultry industry worldwide (See Kibenge (1988), *J. Gen. Virol.*, 69:1757–1775). Infection of susceptible chickens with virulent IBDV strains can lead to a highly contagious immunosuppressive condition known as infectious bursal disease (IBD). Damage caused to the lymphoid follicles of the bursa of Fabricius and spleen can exacerbate infections caused by other agents and reduce a chicken's ability to respond to vaccination as well (See Cosgrove (1962), *Avian Dis.*, 6:385–3894).

IBDV is a member of the Birnaviridae family and its genome consists of two segments of double-stranded RNA (See Dobos et al (1979), *J. Virol.*, 32:593–605). The smaller segment B (about 2800 bp) encodes VP1, the dsRNA polymerase. The larger genomic segment A (about 3000 bp) encodes a 110 kDa precursor polypeptide in a single open reading frame (ORF) that is processed into mature VP2, VP3 and VP4 (See Azad et al (1985), *Virology*, 143:35–44). From a small ORF partly overlapping with the polypeptide ORF, segment A can also encode VP5, a 17-kDa protein of unknown function (See Kibenge et al (1991), *J. Gen. Virol.* 71:569–577).

While VP2 and VP3 are the major structural proteins of the virion, VP2 is the major host-protective immunogen and causes induction of neutralizing antibodies (See Becht et al. (1988) *J. Gen. Virol.,* 69:631–640; Fahey et al. (1989), *J. Gen. Virol.,* 70:1473–1481). VP3 is considered to be a group-specific antigen because it is recognized by monoclonal antibodies (Mabs) directed against VP3 from strains of both serotype 1 and 2 (See Becht et al (1988), *J. Gen. Virol.,* 69:631–640). VP4 is a virus-coded protease and is involved in the processing of the precursor protein (See Jagadish et al. (1988), *J. Virol.,* 62:1084–1087).

In the past, control of IBDV infection in young chickens has been achieved by live vaccination with avirulent strains, or principally by the transfer of maternal antibody induced by the administration of live and killed IBDV vaccines to breeder hens. Unfortunately, in recent years, virulent variant strains of IBDV have been isolated from vaccinated flocks in the United States (See e.g., Snyder et al. (1988), *Avian Dis.,* 32:535–539; Van der Marel et al. (1990), *Dtsch. Tierarztl. Wschr.,* 97:81–83), which drastically undermine the effectiveness of using live vaccination for IBDV.

Efforts to develop a recombinant vaccine for IBDV have also been made, and the genome of IBDV has been cloned (See Azad et al (1985) "Virology", 143:35–44). The VP2 gene of IBDV has been cloned and expressed in yeast (See Macreadie et al. (1990), *Vaccine,* 8:549–552), as well as in recombinant fowlpox virus (See Bayliss et al (1991), *Arch. Virol.,* 120:193–205). When chickens were immunized with the VP2 antigen expressed from yeast, antisera afforded passive protection in chickens against IBDV infection. When used in active immunization studies, the fowlpox virus-vectored VP2 antigen afforded protection against mortality, but not against damage to the bursa of Fabricius.

Newcastle disease virus (NDV) is an enveloped virus containing a linear, single-strand, nonsegmented, negative sense RNA genome. Typically, virus families containing enveloped single-stranded RNA of the negative-sense genome are classified into groups having non-segmented genomes (e.g., Paramyxoviridae and Rhabdoviridae) or those having segmented genomes (e.g., Orthomyxoviridae, Bunyaviridae and Arenaviridae). NDV, together with parainfluenza virus, Sendai virus, simian virus 5, and mumps virus, belongs to the Paramyxoviridae family.

The structural elements of the NDV include the virus envelope which is a lipid bilayer derived from the cell plasma membrane. The glycoprotein, hemagglutinin-neuraminidase (HN) protrude from the envelope allowing the virus to contain both hemagglutinin and neuraminidase activities. The fusion glycoprotein (F), which also interacts with the viral membrane, is first produced as an inactive precursor, then cleaved post-translationally to produce two disulfide linked polypeptides. The active F protein is involved in penetration of NDV into host cells by facilitating fusion of the viral envelope with the host cell plasma membrane. The matrix protein (M), is involved with viral assembly, and interacts with both the viral membrane as well as the nucleocapsid proteins.

The main protein subunit of the NDV nucleocapsid is the nucleocapsid protein (NP) which confers helical symmetry on the capsid. In association with the nucleocapsid are the P and L proteins. The phosphoprotein (P), which is subject to phosphorylation, is thought to play a regulatory role in transcription, and may also be involved in methylation, phosphorylation and polyadenylation. The L gene, which encodes an RNA-dependent RNA polymerase, is required for viral RNA synthesis together with the P protein. The L protein, which takes up nearly half of the coding capacity of the viral genome is the largest of the viral proteins, and plays an important role in both transcription and replication.

The replication of all negative-strand RNA viruses, including NDV, is complicated by the absence of cellular machinery required to replicate RNA. Additionally, the negative-strand genome can not be translated directly into protein, but must first be transcribed into a positive-strand (mRNA) copy. Therefore, upon entry into a host cell, the virus can not synthesize the required RNA-dependent RNA polymerase. The L, P and NP proteins must enter the cell along with the genome on infection. Both the NDV negative strand genomes (vRNAs) and antigenomes (cRNAs) are encapsidated by nucleocapsid proteins; the only unencapsidated RNA species are virus mRNAs. The cytoplasm is the site of NDV viral RNA replication, just as it is the site for transcription. Assembly of the viral components appears to take place at the host cell plasma membrane and mature virus is released by budding.

In U.S. Pat. No. 5,427,791, Ahmad et al. describe the embryonal vaccination against NDV, which requires the modification of the viruses through the use of ethyl methane sulfonate (EMS). However, EMS is a mutagen so that the vaccine prepared by the use of EMS is suspected to act as a mutagen as well, which is undesirable for regular administration of the vaccine. Nevertheless, without the modification with EMS, the NDV vaccine cannot be applied for in ovo vaccination as almost all of the embryos will die upon injection of the eggs with the unmodified virus.

Infectious bronchitis virus (IBV), the prototype of the family Coronaviridae, is the etiological agent of infectious bronchitis (IB). The virus has a single-stranded RNA genome, approximately 20 kb in length, of positive polarity, and is usually about 80–100 nm in size, being round with projecting 20 nm spikes. IBV is the causative agent of an acute, highly contagious disease in chickens of all ages, affecting the respiratory, reproductive and renal systems.

IBV contains three structural proteins: the spike (S) glycoprotein, the membrane glycoprotein, and the nucleocapsid protein. The spike glycoprotein is so called because it is present in the teardrop-shaped surface projections or spikes protruding from the lipid membrane of the virus. The spike protein is believed likely to be responsible for immunogenicity of the virus, partly by analogy with the spike proteins of other corona-viruses and partly by in vitro neutralization experiments (See, e.g., D. Cavanagh et al. (1984), *Avian Pathology,* 13, 573–583). There are two spike glycoproteins, which are S1 (90,000 daltons) and S2 (84,000 daltons). The polypeptide components of the glycopolypeptides S1 and S2 have been estimated after enzymatic removal of oligosaccharides to have a combined molecular weight of approximately 125,000 daltons. It appears that the spike protein is attached to the viral membrane by the S2 polypeptide.

IBV has been wide-spread in countries where an intensive poultry industry has been developed. Young chickens up to 4 weeks of age are most susceptible to IBV, infection leading to high rates of morbidity and to mortality resulting from secondary bacterial infection. Infection also results in a drop in egg production, or failure to lay at full potential, together with an increase in the number of down-graded eggs with thin, misshapen, rough and soft-shells produced, which can have a serious economic effect.

Administering live vaccines to a developing chick in the egg (in-ovo) has proven to be a fast (40,000 eggs per hour), effective (100% of the eggs receive the vaccine), and labor saving ($100,000 per year per hatchery) method to vaccinate baby chicks against certain diseases before they hatch.

Recently, Embrex, Inc. has developed a live viral vaccine called VNF® (Viral Neutralizing Factor). The VNF contains an antibody (immunoglobulin) specific for the virus used in the vaccine. This specific antibody is mixed in an appropriate ratio with the vaccine virus to form a virus-antibody complex (immune complex) vaccine. The amount of the antibody in a complex vaccine is so small that it does not provide passive immunity or neutrialize the vaccine virus. On the other hand, the amount of antibody added to the vaccine virus is enough to delay by several days the normal course of vaccine virus replication.

This delayed vaccine virus replication allows for the safe in ovo administration of moderately attenuated vaccine viruses in young animals. Moderately attenuated vaccine viruses are better at overcoming maternal immunity and at stimulating strong protective immune responses than highly attenuated vaccine viruses. Therefore, the virus-antibody complex vaccine technology allows for the safe hatchery use of vaccine viruses that are not eliminated by maternal antibody. Vaccination in the hatchery (either in ovo or at hatch) is better controlled and more uniform than field vaccination. Thus, the virus-antibody complex vaccine technology improves vaccine efficacy as well as safety.

In the invention to be presented in the following sections, immuno-stimulatory nucleotides, particularly a DNA sequence, specific for avian viral vaccines (collectively "vaccine accelerator factor" and abbreviated as "VAF") will be introduced. The VAF can be either co-administered with or separately administered from the commercially available vaccines. The VAF can be either a single or multiple DNA constructs, each containing a single DNA molecule which is a viral gene or a fragment thereof. Additionally, the VAF can be a multivalent DNA construct, which contains two or more viral genes or fragments thereof linking together in one DNA construct. The viral genes or fragments used in preparation of the VAFs are those that encode viral peptides which are antigenic to and can induce both the humoral and the cellular immune system in a host. The VAFs are preferably applied in ovo in an appropriate quantity.

Although the VAFs share the same advantages as the VNF, i.e., to improve vaccine efficacy as well as safety, the VAFs differ from the antibody used in Embrex VNF. Most importantly, the VAF stimulates immunological responses, such as antibody induction, T-cell activation with cytokine secretion, and the production of cytotoxic T lymphocytes, while the antibody in VNF acts to delay the normal course of vaccine virus replication. The VAF allows the immune system to respond to the live vaccines much faster and enables the live vaccines to generate much higher titres of antibody than without the VAF. Also, the VAF's effect on stimulating the immune response is not influenced by maternal immunity. Thus, the VAF, in sum, improves pre-hatch immune response, which in turn improves life long poultry health and reduces vaccination costs.

Commercial poultry are an extremely important source for food. Through the combined use of VAF and appropriate vaccination program, the potential losses caused by infections of commercial flocks can be minimized.

SUMMARY OF THE INVENTION

The present invention provides a vaccine accelerator factor (VAF), which is a nucleotides- or DNA-containing in ovo immuno-stimulant. The VAF contains one or more DNA constructs. Each of the DNA constructs comprises a DNA molecule and a vector. The DNA molecule comprises at least one gene or a fragment of the gene encoding an antigenic peptide of an avian virus. The VAF stimulates and accelerates a protective immune response of a viral vaccine against the avian virus of which the DNA molecule contains a gene or a fragment thereof.

There are four major kinds of VAFs. The first kind of VAF contains one DNA construct. The DNA molecule of the DNA construct contains one gene or a fragment of this gene encoding an antigenic peptide of an avian virus. This kind of VAF stimulates and accelerate a viral vaccine against the same avian virus. The second kind of VAF also contains one DNA construct. But the DNA molecule of the DNA construct in the second kind of VAF contains more than one viral gene or a fragment thereof In other words, the DNA construct is a "multivalent" DNA VAF where two or more genes or fragments thereof, each from a different avian virus, are linked together with a vector. The multivalent DNA VAF is capable of stimulating and accelerating two or more viral vaccines or a viral vaccine containing two or more viral antigens against the same avian viruses represented in the VAF. The third kind of VAF contains more than one DNA construct. Each of the DNA molecule of the DNA construct in this VAF contains only one gene or a fragment of the gene. In other words, this kind of VAF is a "multiple" DNA VAF. A "multiple" DNA VAF is also capable of stimulating and accelerating two or more viral vaccines or a viral vaccine containing two or more viral antigens against the same avian viruses represented in the VAF. Finally, the fourth kind of VAF contains more than one DNA construct. Each of the DNA molecule of the DNA construct either contains one gene or a fragment thereof or more than one gene or a fragment thereof. In other words, this kind of VAF is a "multiple multivalent" DNA VAF. This multiple multivalent DNA VAF is capable of stimulating and accelerating no less than three viral vaccines or a viral vaccine containing no less than three viral antigens against the same avian viruses as represented in the VAF.

The viral vaccines used in combination with the VAF include, but are not limited to, any commercially available viral vaccines, such as vaccines containing live-virus, inactivated virus, or recombinant DNA viral vaccines. The viral vaccines are administered to the fowl either together with or subsequent to the in ovo injection of the VAF. In a preferred embodiment, a live vaccine at ⅕ volume of the full dose recommended by the manufacturer of the viral vaccine is injected into the fowl post hatch after the fowl eggs receive an in ovo injection of VAF.

The vector of the DNA construct can be a plasmid or a viral carrier. The preferred vector is a plasmid. Examples of the plasmid include, but are not limited to, pcDNA3, pVAX1, pSectag, pTracer, pDisplay, pUC system plasmid (such as pUC7, pUC8, pUC18), and pGEM system plasmid. Alternatively, any plasmid which contains a promoter such as CMV promoter, SV40 promoter, RSV promoter, and β-actin promoter, can also be used for preparing the DNA construct. The most favorable plasmid is pcDNA3. The preferred viral carrier is one of the following viruses: a bacteriophage, SV40, an adenovirus, a polyoma virus, a baculovirus, a herpes virus, a vaccinia virus, or a pox virus.

Examples of the avian virus include, but are not limited to Marek's disease virus (MDV), infectious vursal disease virus (IBDV), Newcastle disease virus (NDV), infectious bronchitis virus (IBV), infectious laryngotracheitis virus (ILTV), avian encephalomyelitis (AEV), avian leukosis virus (ALV), fowlpox virus (FPV), avian paramyxovirus (APV), duck hepatitis virus (DHV), and hemorrhagic enteritis virus (HEV).

The genes contained in the DNA molecules that are particularly suitable for stimulating and accelerating a protective immune response against avian viral diseases include, but are not limited to, the entire of gB gene of Merk's Disease virus (MDV) having the DNA sequence of SEQ ID NO:1 or a fragment thereof; the entire VP2 gene of infectious bursal disease virus (IBDV) having the DNA sequence of SEQ ID NO:2 or a fragment thereof; the entire HN gene of Newcastle disease virus (NDV) having the DNA sequence (which is from bases 6321 to 8319) of SEQ ID NO:3 or a fragment thereof (i.e., SEQ ID NO:3 is the entire genome of the NDV); the entire S1 gene of infectious bronchitis virus (IBV) having the DNA sequence of SEQ ID NO:4 or a fragment thereof; the entire glycoprotein G gene of infectious laryngotracheitis virus (ILTV) having the DNA sequence of SEQ ID NO:5 or a fragment thereof; the entire VP1, VP0, or VP3 gene of avian encephalomyelitis virus (AEV) or a fragment thereof (the VP 1 gene has the DNA sequence of SEQ ID NO:6; the VP0 gene has the DNA sequence of SEQ ID NO:7; and the VP3 gene has the DNA sequence of SEQ ID NO:8); the entire paraglycoprotein G gene of avian parainfluenza virus (APV) having the DNA sequence of SEQ ID NO:9 or a fragment thereof; the entire type A penton base gene of hemorrhagic enteritis virus (HEV) having the DNA sequence of SEQ ID NO:10 or a fragment thereof; and the entire envelope antigen gene of fowlpox virus (FPV) having the DNA sequence of SEQ ID NO:11 or a fragment thereof.

The VAF is preferred to be injected into the egg, particularly in the amniotic fluid of the egg, of a fowl. The egg is preferred to be fertilized for about 17–19 days. The preferred fowl includes chicken, turkey, duck, and goose.

The present invention also provides a method for vaccinating fowl egg, which includes injecting into a fowl egg the VAF as shown above. The VAF is prepared by ligating a DNA molecule to a plasmid or virus carrier to form a DNA construct. For the VAF which contains more than one DNA construct, two or more of the DNA constructs are mixed together. The insertion of the DNA molecule into the vector can be achieved by conventional method, i e., by ligation the DNA molecule with an enzyme such as T4 DNA ligase when both the genes and the desired vector have been cut with the same restriction enzyme(s) as complementary DNA termini are thereby produced. For pcDNA3, the preferred restriction enzymes are BamH1 and EcoR1.

DETAILED DESCRIPTION OF THE INVENTION

Traditional avian vaccines comprise chemically inactivated virus vaccines or modified live-virus vaccines. Inactivated vaccines require additional immunizations, which are not only expensive to produce but also laborious to administer. Further, some infectious virus particles may survive the inactivation process and may cause disease after administration to the animal.

In general, attenuated live virus vaccines are preferred over inactivated vaccines because they evoke an immune response often based on both humoral and cellular reactions. Such vaccines are normally based on serial passage of virulent strains in tissue culture. However, the attenuation process induces mutations of the viral genome, resulting in a population of virus particles heterogeneous with regard to virulence and immunizing properties. In addition, it is well known that the traditional attenuated live virus vaccines can revert to virulence resulting in disease outbreaks in inoculated animals and the possible spread of the pathogen to other animals.

A comprehensive post-hatch vaccination program involves administrations of different vaccines at various times. The vaccination program starts from 1 day of age and lasts up to 65 weeks of age. Many of the vaccines require repeated administrations, i.e., using vaccines of different immunogenic activities or using different route of administration at various times.

However, as vaccine viruses become more and more attenuated and safer for use in eggs as well as in young animals, they also lose the ability to stimulate a quick and strong protective immune response. This problem is compounded in young animals when maternal immunity is present because maternal antibody often interferes with the replication of more highly attenuated vaccine viruses. Thus, the more attenuated vaccine viruses usually do not stimulate protective immunity in individuals with maternal immunity.

In the poultry industry where high levels of maternal immunity is common, maternal antibody interference has usually been addressed by giving several vaccinations during the first few weeks of life. Normally, a highly attenuated vaccine virus is used at hatch and a moderately attenuated virus is used during the second or third week of life. In this manner it is hoped that at least one of the vaccinations is timed correctly so that the individual is vaccinated prior to exposure to the pathogenic agent. This approach has served the poultry industry relatively well for many years, but it is generally accepted that a certain percentage of individuals in a flock are not going to be properly vaccinated. The percentage of improperly vaccinated individuals increases if the secondary vaccinations are not timed correctly for that particular flock's spread of maternal antibody or if the secondary vaccinations are not adminstered properly and uniformly.

Thus, the employment of the VAF to stimulate and accelerate the immune response of a vaccine would be advantageous for the poultry industry. Particularly, the VAF is injected into an egg of a fowl at 17–19 days of fertilization. Because the VAF contains at least a gene or a fragment of the gene capable of expressing an antigenic peptide of an avian virus in ovo, the administration of the VAF to an egg induces an initial immune response against the avian virus.

Also, the administration of the VAF, together with or prior to the administration of the avian viral vaccine(s), substantially improves the efficacy of the immune response generated by the viral vaccine(s). Especially, the dosage of the vaccine used in combination with the use of VAF for achieving the same immune response is far less than that without the administration of the VAF (as low as 20% of the normal dosage). Also, the time period for achieving the same immune response is much shorter when the VAF is used.

Furthermore, it is well known that some of the commercially available viral vaccines, such as the vaccines for infectious bronchitis virus (IB) and Newcastle disease virus (ND), are not suitable for in ovo injection. That is because the vaccine for IB is known to cause embryonic damage, and the vaccine for ND can only be properly stimulated through local muscular injection. The introduction of the VAF to the immunization of these diseases will improve the overall prevention of the diseases.

For the purpose of preparing the VAF, the DNA sequence of a gene need not contain the full length of DNA encoding the polypeptides. In most cases, a fragment of the gene which encodes an epitope region should be sufficient enough for immunization. The DNA sequence of an epitope region can be found by sequencing the corresponding part of other viral strains and comparing them. The major antigenic determinants are likely to be those showing the greatest heterology. Also, these regions are likely to lie accessibly in the conformational structure of the proteins. One or more such fragments of genes encoding the antigenic determinants can be prepared by chemical synthesis or by recombinant DNA technology. These fragments of genes, if desired, can be linked together or linked to other DNA molecules.

Also, the viral genes need not be in DNA. In fact, some of the frequently found avian viral diseases are caused by double- or single-stranded RNA viruses. For example, Marek's disease virus is a double-stranded RNA virus, while infectious bursal disease virus (IBDV), Newcastle disease virus (NDV) and infectious bronchitis virus (IB) are single-stranded RNA viruses. The RNA viral sequences, however, can be reverse-transcribed into DNA using RT-Polymerase chain reaction (RT-PCR) technology and then incorporated into a vector by the conventional recombinant DNA technology.

In addition, because of the degeneracy of the genetic code it is possible to have numerous RNA and DNA sequences that encode a specified amino acid sequence. Thus, all RNA and DNA sequences which result in the expression of a polypeptide having the antibody binding characteristics are encompassed by this invention.

To construct a recombinant VAF, either univalent or multivalent, the DNA sequence of the viral gene can be ligated to other DNA molecules with which it is not associated or linked in nature. Optionally, the DNA sequence of a viral gene can be ligated to another DNA molecule, i.e., a vector, which contains portions of its DNA encoding fusion protein sequences such as β-galactosidase, resulting in a so-called recombinant nucleic acid molecule or DNA construct, which can be used for transformation of a suitable host. Such vector is preferably derived from, e.g., plasmids, or nucleic acid sequences present in bacteriophages, cosmids or viruses.

Specific vectors which can be used to clone nucleic acid sequences according to the invention are known in the art and include either a plasmid or a virus carrier. Examples of the plasmid include, but are not limited to, pBR322, pcDNA3, pVAX1, pSectag, pTracer, pDisplay, pUC system plasmids (e.g., pUC7, pUC8, pUC18), pGEM system plasmids, Bluescript plasmids or any other plasmids where CMV promoter, SV40 promoter, RSV promoter, or β-actin promoter is included. The preferred plasmid is pcDNA3. Examples of the virus carrier include, but are not limited to, bacteriophages (e.g., γ and the M13-derived phages), SV40, adenovirus, polyoma, baculoviruses, herpes viruses (HVT), vaccinia virus, or pox viruses (e.g., fowl pox virus).

The methods to be used for the construction of a recombinant nucleic acid molecule are known to those of ordinary skill in the art. For example, the insertion of the nucleic acid sequence into a cloning vector can easily be achieved by ligation with an enzyme such as T4 DNA ligase when both the genes and the desired cloning vehicle have been cut with the same restriction enzyme(s) so that complementary DNA termini are thereby produced.

Alternatively, it may be necessary to modify the restriction sites so as to produce blunt ends either by digesting the single-stranded DNA or by filling in the recessive termini with an appropriate DNA polymerase. Subsequently, blunt end ligation with an enzyme such as T4 DNA ligase may be carried out. If desired, any restriction site may be produced by ligating linkers onto the DNA termini. Such linkers may comprise specific oligonucleotide sequences that encode restriction site sequences. The restriction enzyme cleaved vector and nucleic acid sequence may also be modified by homopolymeric tailing.

The present invention provides four kinds of VAFs. The first kind is a VAF containing one DNA construct (i.e., univalent VAF), which comprises a DNA molecule and a vector. The DNA molecule contains one DNA sequence (which can be a gene or a fragment of a gene) encoding one antigenic peptide which provide immuno-protection against one avian virus. The second kind of VAF comprises two or more of the kind of the univalent VAF, each carrying a different DNA sequence against a different avaian virus.

The third kind of VAF contains one DNA construct in which the DNA molecule contains two or more genes or gene fragments linked together, each from a different avian virus (i.e., a multivalent VAF or multivalent recombinant VAF). These genes or gene fragments are carried by a useful vector, which can be either a plasmid or a virus carrier. The multivalent recombinant VAF encodes two or more antigenic polypeptides which afford protection against at least two viral diseases including, but not limited to, MD, IBD, ND or IB. The viral genes or gene fragments are operatively attached to the vector in reading frame so that they can be expressed in a host. The different structural DNA sequences carried by the vector may be separated by termination and start sequences so that the proteins can be expressed separately or they may be part of a single reading frame and therefore be produced as a fusion protein by methods known in the art. The fourth kind of VAF is a mixture of the univalent and multivalent DNA VAF.

The viral genes or gene fragments are preferably derived from Marek's disease virus (MDV), infectious bursal disease virus (IBDV), Newcastle disease virus (NDV), infectious bronchitis virus (IBV), infectious laryngotracheitis virus (ILTV), avian encephalomyelitis (AEV), Fowlpox virus (FPV), avian influenza virus (AIV), avian leukosis virus (ALV), duck hepatitis virus B genome, and hemorrhagic enteritis virus (HEV), inserted into a commercially available plasmid.

The preferred DNA sequences include, but are not limited to, the entire of gB gene of Merk's Disease virus (MDV) having the DNA sequence of SEQ ID NO:1 or a fragment thereof; the entire VP2 gene of infectious bursal disease virus (IBDV) having the DNA sequence of SEQ ID NO:2 or a fragment thereof; the entire HN gene of Newcastle disease virus (NDV) having the DNA sequence of SEQ ID NO:3 or a fragment thereof; the entire S1 gene of infectious bronchitis virus (IBV) having the DNA sequence of SEQ ID NO:4 or a fragment thereof.

The DNA sequence encoding the gB polypeptide of MDV has the nucleic acid sequence as SEQ ID NO:1. The DNA sequence contains 3650 bp of linear DNA.

The DNA sequence encoding the VP2 polypeptide of IBDV has the nucleic acid sequence as SEQ ID NO:2. The DNA sequence contains 3004 bp of linear DNA molecule which is reversely transcribed from IBDV's RNA template.

The DNA sequence of the entire genome of NDV contains 15186 bps of DNA, wherein (1) base No. 56 to 1792 encodes NP polypeptide, which is nucleocapsid protein; (2) base No. 1804–3244 encodes P polypeptide, which is a phosphoprotein; (3) base No. 3256–4487 encodes M polypeptide, which is a matrix protein; (4) base No. 4498–6279 encodes F polypeptide, which is a fusion protein; (5) base 6321–8319 encodes HN polypeptide, which is a hemagglutinin-neuraminidase; (6) base No. 8370–15073 encodes L polypeptide, which is a large polymerase protein. The NDV genome has the DNA sequence as SEQ ID NO:3.

The DNA sequence of the S1 polypeptide contains 1611 bp of linear DNA sequence as shown in SEQ ID NO:4, which is reversely transcribed from IBV's RNA templates.

The following examples are illustrative, but not limiting the scope of the present invention. Reasonable variations, such as those occur to reasonable artisan, can be made herein without departing from the scope of the present invention.

I. Materials and Methods (A) Virus and Vaccines

Avian infectious bronchitis virus (IBV), infectious bursal disease (IBD) and Newcastle disease (ND) vaccines were purchased from Intervet Inc.

(B) Viral RNA Isolation and RT-PCR

Two hundred microliter recovered attenuated vaccines (Intervet Inc.) were resolved in iced cold GTC buffer (4 M guanidium isothiocyanate, 25 mM sodium citrate, pH 7.0, 0.5% Sarkosyl, 0.1 M—mercaptoethanol) and sodium acetate (pH 4). An equal volume of phenol-chloroform (1:1) was added and placed on ice for 15 minutes after vortexing. The aqueous phase was collected after centrifuge and the RNA was precipitated with an equal volume of isopropanol. RNA was pelleted by centrifugation at 12000 rpm for 20 min at 4° C. and then suspended in diethylpyrocarbonate (DEPC) treated deionized distill water and stored at −70° C.

(C) Oligonucleotides

Oligonucleotide primers for RT-PCR amplification were purchased from Promega, and were designed according to the genome of the Avian infectious bronchitis virus (Beaudette CK strain), Newcastle disease virus (Lasota strain) and Infectious bursa disease virus respectively. The sequences of the primers used for PCR were:

```
IBS1F'   5' CGGGATCCGCCGCCGCCATGTTGGTAACACCTCTT 3';        (SEQ ID NO:12)
IBS1R'   5' CGGAATTCTTAACGTCTAAAACGACGTGT 3';              (SEQ ID NO:13)
NPF F'   5' CGGGATCCGCCGCCGCCATGGGCTCCAGACCTTCTACC 3';     (SEQ ID NO:14)
NDF R'   5' CCGCTCGAGTTACATTTTTGTAGTGGCTCTCATT 3';         (SEQ ID NO:15)
NDHN F'  5' CGGGATCCGCCGCCGCCATGGACCGCGCCGTTAGGCAAG 3';    (SEQ ID NO:16)
NDHN R'  5' GCTCTAGATTACTCAACTAGCCAGACCTG 3';              (SEQ ID NO:17)
IBDVP2F' 5' CGGGATCCGCCGCCGCCATGACAAACCTGCAAGAT 3';        (SEQ ID NO:18)
IBDVP2R' 5' CGGAATTCTTACCTTATGGCCCGGATTAT 3'.              (SEQ ID NO:19)
```

(D) Reverse Transcription Polymerase Reaction (RT-PCR)

Reverse transcription of IBV, NDV and IBDV RNA were carried out at 42° C. for 30 min in 2.5×Taq buffer (200 mM NaCl, 15 mM Tris-HCl, pH7.4, 15 mM $MgCl_2$, 15 mM β—mercaptoethanol, and 0.25 mM each of dATP, dCTP, dGTP, and dTTP). In addition to the Taq buffer, the reaction mixture (40 μl) also contained viral RNA, 2.4 U of avian mycloblastosis virus (AMV) reverse transcriptase (Promega), 16 U of RNasin (Promega), and 0.01 nmol reverse primer (IBDVP2R, NDF F, NDHN F or IBSIR). The final volume of the reaction mixture was 40 μl. After reverse transcription, the following reagents were added to the reverse transcription mixture: 0.02 nmol of each nucleotide triphosphate (dATP, dCTP, dGTP, dTTP), 0.01 nmol of forward primer (IBDVP2F, NDF R, NDHN R or IBS1F) and 1.5 U of Taq DNA polymerase (Strategene). Water was then added to a final volume of 100 μl. The reaction was carried out for 32 cycles in a Thermal Cycler (Perkin Elmer-Cetus). Each PCR cycle consisted of 1 min of denaturation at 94° C., 1 min of annealing at 57° C., and 2 min of DNA chain elongation at 72° C.

(E) Preparation of DNA Constructs

The plasmids pCMV-VP2, pCMV-S1, pCMV-NDF and pCMV-NDHN were constructed with the VP2, S1, NDF and NDHN genes from IBD vaccine, IBV vaccine and NDV vaccine respectively, placed downstream of the commercial plasmid pcDNA3. (Invitrogen, U.S.A.). All of the genes were inserted into the pcDNA3 vector using restriction enzymes BamH1, EcoR1, XbaI and XhoI (underlined characters in the sequence of the primers). Sequences of the all genes in the pcDNA3 vector were verified by sequencing in both directions.

(F) Preparation of DNA and DNA Delivery

The quantity of plasmid DNA that had been purified by affinity chromatography (Qiagen. Inc.) was determined by spectrophotometric measurements at 260 and 280 nm. The DNA in aliquots to 100 μg was suspended in 100 μl of PBS (0.14M NaCl, 10 mM sodium phosphate, pH 7.4). For DNA delivery, 1 cc syringe with a 20 gauge 1 and ½ inch needle were used. For the in-ovo groups, the embryos (18-day-old fertilized and developing eggs from the setting trays) were injected with 0.1 milliliters of VAF (100 μg) into the large end of each egg through the air cell with a needle. The eggs were then transferred into the hatchery where they remained until they hatched at about 21 days of age. For the IM (Intramuscular), all of the vaccines ( ⅕ dose of live vaccines) were injected into the chicken's thoracic muscle at 10 days post hatchery.

II. Experimental Design

Specific Pathogen Free (SPF) fertilized eggs (n=60) were randomized into 12 groups. All groups (five eggs each group), all eggs were given 100 μl in volume each. 100 μg pCMV-NDF+100 μg pCMV-NDHN mixture was injected in each egg of group A, 100 μg pCMV-S1 was injected in each egg of group B, 100 μg pCMV-VP2 was injected in each egg of group C, 100 μg pCMV-NDF+100 μg pCMV-NDHN+ 100 μg pCMV-S1(ND+IB) was injected in each egg of group D, 100 μg pCMV-NDF+100 μg pCMV-NDHN+100 μg pCMV-VP2 (ND+IBD) was injected in each egg of group E, 100 μg pCMV-VP2+100 μg pCMV-VP2 mixture (IB+IBD) was injected in each egg of group F, 100 μg pCMV-NDF+ 100 μg pCMV-NDHN+100 μg pCMV-S1+ 100 μg pCMV-VP2 mixture (ND+IB+IBD) was injected in each egg of group G, one dose of commercialized in-ovo IBD vaccine (Embrex, Inc) was injected in each egg of group H as positive control, 100 ul PBS was injected in each egg of group I, J, K and L. All chickens in this experiment were given 100 μl in volume ( ⅕ dose of live vaccines), injected into the chicken's thoracic muscle each at 10 days post hatchery. Chickens in group A and I were injected with NDV vaccine, group B and J were injected with IBV vaccine, group C and K were injected with IBDV vaccine, group D were injected with the mixture of NDV+IB vaccines, group E were injected with the mixture of NDV+IBD vaccines, group F were injected with the mixture of IB+IBD vaccines and group G and L were injected with the mixture of NDV, IB and IBD vaccines.

III. Manual In ovo Injection Procedure:

The in ovo injection could either be performed by automatic in ovo vaccination system (such as Embrex Inovoject® system) or by manual procedure. A manual in ovo procedure was described as follows:

1. The eggs were candled to remove infertile, contaminated, and/or upside down eggs. Also, dirty eggs were moved to avoid bacterial contamination during the injection.

2. The top of the air cell of each egg was sanitized by a diluted bleach solution (prepared by mixing a 10% solution of household bleach in distilled water to reach a final concentration of 0.5% hypochlorite). Preferably, the diluted bleach solution was prepared fresh and mixed just before use. A cotton swab soaked in the diluted bleach was used to wipe the surface on top (air cell) of the egg. Alternatively, iodine could be used to replace the diluted bleach, although the diluted bleach was more effective. If clean eggs were used, there was no need to clean the eggs with the diluted bleach solution.

3. Once the bleach solution has dried on the eggs surface (about 5 minutes), the eggs were sprayed with 70% isopropyl alcohol. After the 70% isopropyl alcohol was dried, a hole was punched in the air cell end on top of the egg by inserting an 18 gauge 1 and ½ inch needle through a rubber stopper so that ¼ to ½ inch of the needle tip emerges from the stopper. This hole would be used to insert the needle when injecting the vaccine. When vaccine or VAF was inserted into the egg, the needle and syringe must be straight up and down (not at an angle). The embryo was not hurt by this way so that the fowl could hatch normally.

4. The VAF was preferably injected into the egg by a 1 cc syringe with a 20 gauge 1 inch needle. For multiple or multiple multivalent VAFs, it was important that the DNA constructs were mixed under sterile conditions. The sterility of the VAF could be confirmed by sampling it before and after the injection by putting ½ mL of the VAF onto a general purpose medium such as blood agar or Trypticase soy agar to determine the presence of bacteria.

6. For in ovo live vaccine injection, normally, 100 μL of the commercially available vaccine was injected into an egg (which constituted 100% full volume). If the live vaccine was used in connection with the VAF, less volume (at low as 20 μL) of the vaccine could be used to achieve the same titer in the young animals.

IV. Serology Detection

All of the serum samples from a fowl were collected at 10 days (injected with low dose live vaccines at the same time), 17 days, 24 days and 31 days post hatchery. The antibody titers were detected by ELISA using IB, IBD and NDV antibody test kits which purchased from IDEXX Laboratories, Inc. All of the samples were detected duplicated. Dilute test samples five hundred fold (1:500) with sample diluents prior to being assayed. The test procedure was applied according to the kit's manual. For the assay to be valid, measure and record absorbance values at 650 nm, A (650). The relative level of antibody in the unknown was determined by calculating the sample to positive (S/P) ratio. Endpoint titers were calculated using the formula:

$$\mathrm{Log}_{10}\ \mathrm{Titer}=1.09(\mathrm{Log}_{10}\ S/P)+3.36$$

IV. Results

As shown in Table 1, the results demonstrated that, for the detection of anti-IBD antibodies, the IBDV recombinant antigen VP2 DNA construct (i.e., a single, monovalent DNA contruct-containing VAF) could be expressed and played the role of primary stimulation of IBVD immunization. The titers increased rapidly after a low dose vaccine booster. The titers of group C, E, F and G at 17 days post hatchery (i.e., 7 days post IM injection) were significantly higher than those of group K and L. Most importantly, the expression of IBDV antigen was not interfered by other monovalent VAFs (NDV and IBV). The same results were also applied to IB and NDV VAFs. The titers of group B, D, F and G were higher than those of group J and L at 17 days post hatchery (Table 2) and the titers of group A, D, E and G were higher than those of group I and L at 17 days post hatchery (Table 3). The only unpredicted result was the anti-NDV titer could not be highly induced by the triple valent VAF (Table 3, group G), but anti-IBD and anti-IB could (Tables 1 and 2, group G).

TABLE 1

Serum Samples Detected by IDEXX IBD Antibody Test Kit (Ab Titers Correspond to the Average Titers ± SD)
Immunization and Sample Collection Schedule (days)

| Animal Group | 10 Days PH* | 17 Days PH | 24 Days PH | 31 Days PH |
|---|---|---|---|---|
| C(IBD) | —** | 4535 ± 1267 | 16623 ± 3105 | 21254 ± 3852 |
| E(IBD + ND) | — | 1685 ± 655 | 17339 ± 2185 | 19041 ± 2967 |
| F(IBD + IB) | — | 8252 ± 2205 | 10057 ± 1295 | 17561 ± 2006 |
| G(IBD + IB + ND) | — | 9111 ± 1701 | 13127 ± 1763 | 16694 ± 2134 |
| H(IBD positive) | 6553 ± 851 | 13025 ± 2131 | 18015 ± 1592 | 18853 ± 2614 |
| K(PBS/IBD) | — | — | 1853 ± 302 | 17002 ± 2965 |
| L(PBS/IBD + IB + ND) | — | — | 6923 ± 1168 | 18063 ± 2531 |

*PH: post hatchery
**—: average titers less than 396 (be considered negative by IDEXX kit)

TABLE 2

Serum Samples Detected by IDEXX IB Antibody test kit (Ab Titers Correspond to the Average Titers ± SD
Immunization and Sample Collection Schedule (days)

| Animal Group | 10 Days PH* | 17 Days PH | 24 Days PH | 31 Days PH |
|---|---|---|---|---|
| B(IB) | —** | 441 ± 117 | 2426 ± 264 | 3214 ± 877 |
| D(IB + ND) | — | 586 ± 182 | 805 ± 221 | 1988 ± 501 |
| F(IB + IBD) | — | 509 ± 89 | 685 ± 186 | 1192 ± 237 |
| G(IBD + IB + ND) | — | 499 ± 81 | 688 ± 78 | 2551 ± 531 |
| J(PBS/IB) | — | — | 485 ± 76 | 1662 ± 441 |
| L(PBS/IBD + IB + ND) | — | — | 819 ± 202 | 1332 ± 488 |

*PH: post hatchery
**—: average titers less than 396 (be considered negative by IDEXX kit)

TABLE 3

Serum Samples Detected by IDEXX ND Antibody Test Kit (Ab Titers Correspond to the Average Titers ± SD).
Immunization and Sample Collection Schedule (days)

| Animal Group | 10 Days PH* | 17 Days PH | 24 Days PH | 31 Days PH |
|---|---|---|---|---|
| A(ND) | — | 466 ± 101 | 2394 ± 456 | 8103 ± 2198 |
| D(ND + IB) | — | 706 ± 140 | 1778 ± 378 | 6811 ± 2206 |
| E(ND + IBD) | — | 517 ± 104 | 3021 ± 411 | 5991 ± 1695 |
| G(IBD + IB + ND) | — | — | — | 783 ± 201 |
| I(PBS/ND) | — | — | 1853 ± 324 | 3912 ± 304 |
| L(PBS/IBD + IB + ND) | — | — | 4027 ± 662 | 5807 ± 1996 |

*PH: post hatchery
**—: average titers less than 396 (be considered negative by IDEXX kit)

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

I claim:

1. A method for vaccinating a fowl against viral infection comprising:

(a) injecting into an amniotic fluid of a fowl egg a vaccine accelerator factor (VAF) comprising:

one DNA construct; said DNA construct comprising a DNA molecule and a vector; said DNA molecule comprising one gene or fragment thereof encoding an antigenic peptide of an avian virus;

wherein said DNA construct of said VAF stimulates and accelerates a protective immune response of a viral vaccine against said avian virus where said gene or fragment thereof is coded from;

wherein said vector is a plasmid or a viral carrier; wherein said viral carrier is one selected from the group consisting of a bacteriophage, an SV40, an adenovirus, a polyoma virus, a baculovirus, a herpes virus, a vaccinia virus, and a pox virus;

wherein said viral vaccine is selected from the group consisting of an attenuated live virus vaccine and an inactivated virus vaccine; and (b) injecting said viral vaccine into said fowl egg before hatch or into said fowl egg at hatch or into the fowl hatched from said egg after hatch at an amount equalled to about 20% of a full dose of said viral vaccine to achieve a same titer as said full dose of said viral vaccine in said fowl.

2. The method according to claim 1, wherein said egg is fertilized for about 17–19 days.

3. The method according to claim 1, wherein said avian virus is one selected from the group consisting of Marek's disease virus (MDV), infectious bursal disease virus (IBDV), Newcastle disease virus (NDV), infectious bronchitis virus (IBV), infectious laryngotracheitis virus (ILTV), avian encephalomyelitis (AEV), avian leukosis virus (ALV), fowlpox virus (FPV), avian parainfluenza virus (APV), duck hepatitis virus (DHV), and hemorrhagic enteritis virus (HEV).

4. The method according to claim 1, wherein said gene of said DNA molecule is an entire HN gene of Newcastle disease virus (NDV) having the DNA sequence of bases 6321 to 8319 in SEQ ID NO:3.

5. The method according to claim 1, wherein said fowl is a chicken.

6. The method according to claim 1, wherein said fowl is a turkey.

7. A method for vaccinating a fowl against viral infection comprising:

(a) injecting into an amniotic fluid of a fowl egg a vaccine accelerator factor (VAF) comprising:

two or more DNA constructs; each of said DNA constructs comprising a DNA molecule and a vector; said DNA molecule comprising one gene or fragment thereof encoding an antigenic peptide of an avian virus;

wherein each of said DNA constructs of said VAF stimulates and accelerates a protective immune response of a viral vaccine against said avian virus where said gene or fragment thereof is coded from;

wherein said vector is a plasmid or a viral carrier; wherein said viral carrier is one selected from the group consisting of a bacteriophage, an SV40, an adenovirus, a polyoma virus, a baculovirus, a herpes virus, a vaccinia virus, and a pox virus, wherein said viral vaccine is selected from the group consisting of an attenuated live virus vaccine and an inactivated virus vaccine; and (b) injecting said viral vaccine into said fowl egg before hatch or into said fowl egg at hatch or into the fowl hatched from said egg after hatch at an amount equalled to about 20% of a full dose of said viral vaccine to achieve a same titer as said full dose of said viral vaccine in said fowl.

8. The method according to claim 7, wherein said egg is fertilized for about 17–19 days.

9. The method according to claim 7, wherein said avian virus is one selected from the group consisting of Marek's disease virus (MDV), infectious bursal disease virus (IBDV), Newcastle disease virus (NDV), infectious bronchitis virus (IBV), infectious laryngotracheitis virus (ILTV), avian encephalomyelitis (AEV), avian leukosis virus (ALV), fowlpox virus (FPV), avian parainfluenza virus (APV), duck hepatitis virus (DHV), and hemorrhagic enteritis virus (HEV).

10. The method according to claim 7, wherein said gene of said DNA molecule is an entire HN gene of Newcastle disease virus (NDV) having the DNA sequence of bases 6321 to 8319 in SEQ ID NO:3.

11. The method according to claim 7, wherein said fowl is a chicken.

12. The method according to claim 7, wherein said fowl is a turkey.

13. A method for vaccinating a fowl against viral infection comprising:

(a) injecting into an amniotic fluid of a fowl egg a vaccine accelerator factor (VAF) comprising:

one DNA construct; said DNA construct comprising a DNA molecule and a vector; said DNA molecule comprising two or more genes or fragments thereof, each of said genes or fragments thereof encoding an antigenic peptide of an avian virus;

wherein each of said genes or fragment thereof stimulates and accelerates a protective immune response of a viral vaccine against said avian virus from which each of said genes or fragments thereof is coded from;

and wherein said vector is a plasmid or a viral carrier; wherein said viral carrier is one selected from the group consisting of a bacteriophage, an SV40, an adenovirus, a polyoma virus, a baculovirus, a herpes virus, a vaccinia virus, and a pox virus;

wherein said viral vaccine is selected from the group consisting of an attenuated live virus vaccine and an inactivated virus vaccine; and (b) injecting said viral vaccine into said fowl egg before hatch or into said fowl egg at hatch or into the fowl hatched from said egg after hatch at an amount equalled to about 20% of a full dose of said viral vaccine to achieve a same titer as said full dose of said viral vaccine in said fowl.

14. The method according to claim 13, wherein said egg is fertilized for about 17–19 days.

15. The method according to claim 13, wherein said avian virus is one selected from the group consisting of Marek's disease virus (MDV), infectious bursal disease virus (IBDV), Newcastle disease virus (NDV), infectious bronchitis virus (IBV), infectious laryngotracheitis virus (ILTV), avian encephalomyelitis (AEV), avian leukosis virus (ALV), fowlpox virus (FPV), avian parainfluenza virus (APV), duck hepatitis virus (DHV), and hemorrhagic enteritis virus (HEV).

16. The method according to claim 13, wherein one of said genes of said DNA molecule is an entire HN gene of Newcastle disease virus (NDV) having the DNA sequence of bases 6321 to 8319 in SEQ ID NO:3.

17. The method according to claim 13, wherein said fowl is a chicken.

18. The method according to claim 13, wherein said fowl is a turkey.

19. A method for vaccinating a fowl against viral infection comprising:

(a) injecting into an amniotic fluid of a fowl egg a vaccine accelerator factor (VAF) comprising:

two or more DNA constructs; each of said DNA constructs comprising a DNA molecule and a vector; said DNA molecule comprising two or more genes or fragments thereof, each of said genes or fragments thereof encoding an antigenic peptide of an avian virus;

wherein each of said genes or fragments thereof stimulates and accelerates a protective immune response of a viral vaccine against said avian virus from which said gene or fragment thereof is coded from;

wherein said vector is a plasmid or a viral carrier; wherein said viral carrier is one selected from the group consisting of a bacteriophage, an SV40, an adenovirus, a polyoma virus, a baculovirus, a herpes virus, a vaccinia virus, and a pox virus;

wherein said viral vaccine is selected from the group consisting of an attenuated live virus vaccine and an inactivated virus vaccine; and (b) injecting said viral vaccine into said fowl egg before hatch or into said fowl egg at hatch or into the fowl hatched from said egg after hatch at an amount equalled to about 20% of a full dose of said viral vaccine to achieve a same titer as said full dose of said viral vaccine in said fowl.

20. The method according to claim 19, wherein said egg is fertilized for about 17–19 days.

21. The method according to claim 19, wherein said avian virus is one selected from the group consisting of Marek's disease virus (MDV), infectious bursal disease virus (IBDV), Newcastle disease virus (NDV), infectious bronchitis virus (IBV), infectious laryngotracheitis virus (ILTV), avian encephalomyelitis (AEV), avian leukosis virus (ALV), fowlpox virus (FPV), avian parainfluenza virus (APV), duck hepatitis virus (DHV), and hemorrhagic enteritis virus (HEV).

22. The method according to claim 19, wherein said gene of said DNA molecule is an entire HN gene of Newcastle disease virus (NDV) having the DNA sequence of bases 6321 to 8319 in SEQ ID NO:3.

23. The method according to claim 19, wherein said fowl is a chicken.

24. The method according to claim 19, wherein said fowl is a turkey.

* * * * *